(12) United States Patent
Valdez et al.

(10) Patent No.: US 7,419,799 B2
(45) Date of Patent: Sep. 2, 2008

(54) COMPOSITIONS AND METHODS FOR THE TREATMENT OF IMMUNE RELATED DISEASES

(75) Inventors: Patricia A. Valdez, San Francisco, CA (US); Austin L. Gurney, Belmont, CA (US); Iqbal Grewal, Fremont, CA (US)

(73) Assignee: Genetech, Inc., South San Francisco, CA (US)

( * ) Notice: Subject to any disclaimer, the term of this patent is extended or adjusted under 35 U.S.C. 154(b) by 614 days.

(21) Appl. No.: 10/136,574

(22) Filed: Apr. 29, 2002

(65) Prior Publication Data

US 2003/0099661 A1    May 29, 2003

(51) Int. Cl.
*C07H 21/04* (2006.01)
*A61K 39/00* (2006.01)
*C12P 21/06* (2006.01)
*C12N 15/00* (2006.01)
*C12N 1/00* (2006.01)
*C12N 1/20* (2006.01)
*C12N 5/06* (2006.01)
*C07K 1/00* (2006.01)

(52) U.S. Cl. .................. 435/69.1; 536/23.5; 424/185.1; 435/320.1; 435/252.33; 435/254.2; 435/358; 530/350

(58) Field of Classification Search ................ 435/69.1, 435/320.1, 325; 530/350
See application file for complete search history.

(56) References Cited

U.S. PATENT DOCUMENTS

| | | | |
|---|---|---|---|
| 5,194,596 A * | 3/1993 | Tischer et al. | 530/399 |
| 5,350,836 A * | 9/1994 | Kopchick et al. | 530/399 |
| 2003/0092017 A1 * | 5/2003 | Finger | 435/6 |
| 2004/0005317 A1 * | 1/2004 | Dedera et al. | 424/144.1 |
| 2005/0027114 A1 * | 2/2005 | Kuo et al. | 536/23.5 |
| 2005/0260714 A1 * | 11/2005 | Agarwal et al. | 435/69.1 |

FOREIGN PATENT DOCUMENTS

WO    WO 01/55336 A2    8/2001

OTHER PUBLICATIONS

Bottino et al., J. Exp. Med. 2001, vol. 193(3), pp. 235-246.*
Parolini, et al., X-linked lymphoproliferative disease. 2B4 molecules displaying inhibitory rather than activating function are responsible for the inability of natural killer cells to kill Epstein-Barr virus-infected cells. Aug. 7, 2000;192(3):337-46.*
Miyata et al., Nucleotide sequence divergence and functional constraint in mRNA evolution. Proc Natl Acad Sci U S A. Dec. 1980;77(12):7328-32.*
Bowie, et al., Deciphering the message in protein sequences: tolerance to amino acid substitutions.Science. Mar. 16, 1990;247(4948):1306-10.*
Wells et al., Additivity of mutational effects in proteins. Biochemistry. Sep. 18, 1990;29(37):8509-17.*
Benjamin et al. A plasticity window for blood vessel remodelling is defined by pericyte coverage of the performed endothelial network and is regulated by PDGF-B and VEGF. Development. May 1998; 125(9):1591-8.*
Vukicevic et al. Induction of nephrogenic mesenchyme by osteogenic protein 1 (bone morphogenic protein 7). PNAS USA. Aug. 20, 1996; 93:9021-6.*
Brenner. Errors in genome annotation. Trends Genet. Apr. 1999;15(4):132-3.*
Skolnick et al. From genes to protein structure and function: novel applications of computational approaches in the genomic era. Trends Biotechnol. Jan. 2000;18(1)34-9.*
Bork P. Powers and pitfalls in sequence analysis: the 70% hurdle. Genome Research. Apr. 2000; 10(4):398-400.*
Doerks et al. Protein annotation: detective work for function prediction. Trends Genet. Jun. 1998; 14(6):248-50.*
Bork et al. Go hunting in sequence databases but watch out for the traps. Trends Genet. Oct. 1996; 12(10):425-7.*
Aversa et al., "Engagement of the Signaling Lymphocytic Activation Molecule (SLAM) on Activated T Cells Results in IL-2 Independent, Cyclosporin A Sensitive T Cell Proliferation and IFN-γ Production." *J. Immunol.* 158(9) : 4036-4044 (1997).
Aversa et al., "SLAM and its Role in T Cell Activation and Th Cell Responses." *Immunol. Cell. Bio.* 75 (2) : 202-205 (1997).
Carreno and Collins., "The B7 Family of Ligands and Its Receptors: New Pathways for Costimulation and Inhibition of Immune Responses." *Ann. Rev. Immunol.* 20 : 29-53 (2002).
Castro et al., "Molecular and Functional Characterization of Mouse Signaling Lymptocytic Activation Molecule (SLAM) : Differential Expression and Responsiveness in Th1 and Th2 Cells." *J. Immunol.* 163 (11) : 5860-5870 (1999).
Cocks et al., "A Novel Receptor Involved in T-Cell Activation." *Nature.* 376 (6537) : 260-263 (Jul. 1995).
Gell and Coombs, eds. *Clinical Aspects of Immunology.*, second edition. Oxford:Blackwell Scientific Publications (1968).
Howie et al., "Molecular Dissection of the Signaling and Costimulatory Functions of CD150 (SLAM) : CD150/SAP Binding and CD150-Mediated Costimulation." *Blood.* 99 (3) : 957-965 (2002).
Latour et al., "Regulation of SLAM-Mediated Signal Transduction by SAP, the X-Linked Lymphoproliferative Gene Product." *Nature Immunology*, 2 (8) : 681-690 (Aug. 2001).
Lewis et al., "Distinct Interactions of the X-Linked Lymphoproliferative Syndrome Gene Product SAP with Cytoplasmic Domains of Members of the CD2 Receptor Family." *Clin. Immunol.* 100 (1) : 15-23 (2001).

(Continued)

*Primary Examiner*—Gary B. Nickol
*Assistant Examiner*—Cherie M Woodward
(74) *Attorney, Agent, or Firm*—Mark T. Kresnak; Elizabeth M. Barnes; Ginger R. Greger, Esq.

(57) ABSTRACT

The present invention relates to compositions containing a novel protein and methods of using those compositions for the diagnosis and treatment of immune related diseases.

6 Claims, 10 Drawing Sheets

OTHER PUBLICATIONS

Mavaddat et al., "Signaling Lymphocytic Activation Molecule (CDw150) is Homophilic but Self-Associates with Very Low Affinity." *J. Bio. Chem.* 275 (36) : 28100-28109 (2000).

Morra et al., "Characterization of SH2D1A Missorise Mutations Identified in X-Linked Lymphoproliferative Disease Patients." *J. Bio. Chem.* 276 (39) : 36809-36816 (2001).

Nichols et al., 'SAP: Natural Inhibitor or Grand SLAM of T Cell Activation? *Nature Immunology.* 2 (8) : 665 666 (Aug. 2001).

Rich and Myszka., "Advances in Surface Plasmon Resonance Biosensor Analysis." *Curr. Opin, Biotech*, 11:54-61 (2000).

Shlapatska et al., "CD150 Association with Either the SH2-Containing Inositol Phosphatase or the SH2-Containing Protein Tyrosine Phosphatase is Regulated by the Adaptor Protein SH2D1A." *J. Immunol.* 166 (9) : 5480-5487 (2001).

* cited by examiner

FIGURE 1

CAGAAGGGCAAAAACATTGACTGCCTCAAGGTCTCAAGCACCAGTCTTCACCGCGGAAAG
CATGTTGTGGCTGTTCCAATCGCTCCTGTTTGTCTTCTGCTTTGGCCCAGGGAATGTAGT
TTCACAAAGCAGCTTAACCCCATTGATGGTGAACGGGATTCTGGGGGAGTCAGTAACTCT
TCCCCTGGAGTTTCCTGCAGGAGAGAAGGTCAACTTCATCACTTGGCTTTTCAATGAAAC
ATCTCTTGCCTTCATAGTACCCCATGAAACCAAAAGTCCAGAAATCCACGTGACTAATCC
GAAACAGGGAAAGCGACTGAACTTCACCCAGTCCTACTCCCTGCAACTCAGCAACCTGAA
GATGGAAGACACAGGCTCTTACAGAGCCCAGATATCCACAAAGACCTCTGCAAAGCTGTC
CAGTTACACTCTGAGGATATTAAGACAACTGAGGAACATACAAGTTACCAATCACAGTCA
GCTATTTCAGAATATGACCTGTGAGCTCCATCTGACTTGCTCTGTGGAGGATGCAGATGA
CAATGTCTCATTCAGATGGGAGGCCTTGGGAAACACACTTTCAAGTCAGCCAAACCTCAC
TGTCTCCTGGGACCCCAGGATTTCCAGTGAACAGGACTACACCTGCATAGCAGAGAATGC
TGTCAGTAATTTATCCTTCTCTGTCTCTGCCCAGAAGCTTTGCGAAGATGTTAAAATTCA
ATATACAGATACCAAAATGATTCTGTTTATGGTTTCTGGGATATGCATAGTCTTCGGTTT
CATCATACTGCTGTTACTTGTTTTGAGGAAAGAAGAGATTCCCTATCTTTGTCTACTCA
GCGAACACAGGGCCCCGCAGAGTCCGCAAGGAACCTAGAGTATGTTTCAGTGTCTCCAAC
GAACAACACTGTGTATGCTTCAGTCACTCATTCAAACAGGGAAACAGAAATCTGGACACC
TAGAGAAATGATACTATCACAATTTACTCCACAATTAATCATTCCAAAGAGAGTAAACC
CACTTTTTCCAGGGCAACTGCCCTTGACAATGTCGTGTAAGTTGCTGAAAGGCCTCAGAG
GAATTCGGGAATGACACGTCTTCTGATCCCATGAGACAGAACAAAGAACAGGAAGCTTGG
TTCCTGTTGTTCCTGGCAACAGAATTTGAATATCTAGGATAGGATGATCACCTCCAGTCC
TTCGGACTTAAACCTGCCTACCTGAGTCAAACACCTAAGGATAACATCATTTCCAGCATG
TGGTTCAAATAATATTTTCCAATCCACTTCAGGCCAAAACATGCTAAAGATAACACACCA
GCACATTGACTCTCTCTTTGATAACTAAGCAAATGGAATTATGGTTGACAGAGAGTTTAT
GATCCAGAAGACAACCACTTCTCTCCTTTTAGAAAGCAGCAGGATTGACTTATTGAGAAA
TAATGCAGTGTGTTGGTTACATGTGTAGTCTCTGGAGTTGGATGGGCCCATCCTGATACA
AGTTGAGCATCCCTTGTCTGAAATGCTTGGGATTAGAAATGTTTCAGATTTCAATTTTTT
TTCAGATTTTGGAATATTTGCATTATATTTAGCGGTTGAGTATCCAAATCCAAAAATCCA
AAATTCAAAATGCTCCAATAAGCATTTCCCTTGAGTTTCATTGATGTCGATGCAGTGCTC
AAAATCTCAGATTTTGGAGCAATTTGGATATTGGATTTTTGGATTTGGGATGCTCAACTT
GTACAATGTTTATTAGACACATCTCCTGGGACATACTGCCTAACCTTTTGGAGCCTTAGT
CTCCCAGACTGAAAAAGGAAGAGGATGGTATTACATCAGCTCCATTGTTTGAGCCAAGAA
TCTAAGTC

FIGURE 2

```
MLWLFQSLLFVFCFGPGNVVSQSSLTPLMVNGILGESVTLPLEFPAGEKVNFITWLFNET
SLAFIVPHETKSPEIHVTNPKQGKRLNFTQSYSLQLSNLKMEDTGSYRAQISTKTSAKLS
SYTLRILRQLRNIQVTNHSQLFQNMTCELHLTCSVEDADDNVSFRWEALGNTLSSQPNLT
VSWDPRISSEQDYTCIAENAVSNLSFSVSAQKLCEDVKIQYTDTKMILFMVSGICIVFGF
IILLLLVLRKRRDSLSLSTQRTQGPAESARNLEYVSVSPTNNTVYASVTHSNRETEIWTP
RENDTITIYSTINHSKESKPTFSRATALDNVV
```

Signal peptide:

1-13

Transmembrane domain:

228-247

N-glycosylation site.

58-62
     87-91
     137-141
     144-148
     161-165
     178-182
     203-207
     281-285
     303-307
     313-317 cAMP- and cGMP-dependent protein kinase phosphorylation site.

251-255

Tyrosine kinase phosphorylation site.

100-108
     186-194

N-myristoylation site.

17-23
     105-111
     170-176

Amidation site.

82-86

Immunoglobulin domain
    35-111
    146-197

SAP motif
    283-288
    307-312

FIGURE 4

| Cell line | Cell type | Expression |
|---|---|---|
| Jurkat | T cell leukemia | ++ |
| MOLT3 | T cell leukemia | + |
| MOLT4 | T cell leukemia | + |
| Raji | Burkitt's lymphoma | ++ |
| Ramos | Burkitt's lymphoma | ++ |
| Daud | Burkitt's lymphoma | ++ |
| VMI2 | B lymphocyte | +/- |
| U937 | B cell leukemia | - |
| RPMI8888 | B cell leukemia | + |
| HL60 | Promyelocytic leukemia | - |
| IM9 | Multiple myeloma (B lymphoblast) | +/- |
| OPM2 | Multiple myeloma | - |
| U288 | Multiple myeloma | ++ |
| MDA231 | Breast adenocarcinoma | - |
| THP-1 | Monocyte | - |
| HCT116 | Colon carcinoma | - |
| DU145 | Prostate carcinoma | - |
| L8174T | Colorectal adenocarcinoma | - |
| 293 | Kidney epithelial | - |
| SW620 | Colorectal adenocarcinoma | - |
| A873 | Rhabdomyosarcoma | - |
| LOVO | Colorectal adenocarcinoma | - |

FIGURE 9
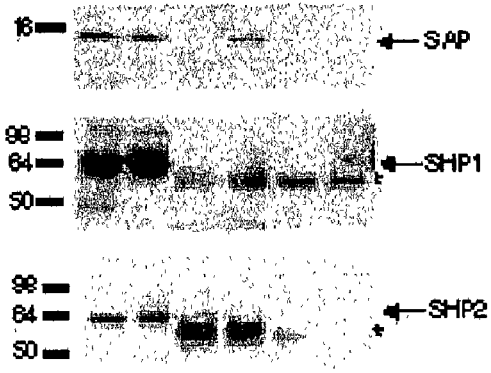
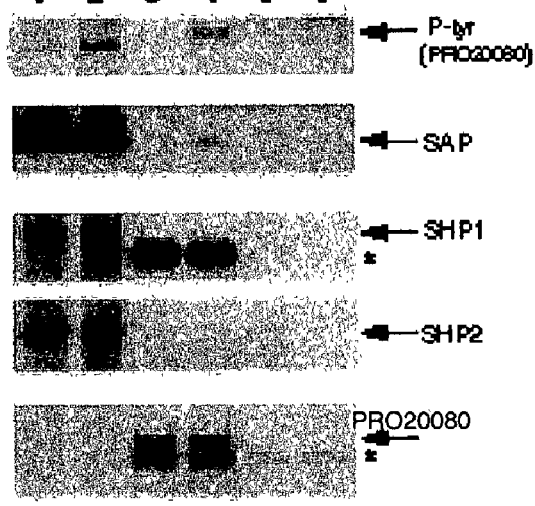

COMPOSITIONS AND METHODS FOR THE TREATMENT OF IMMUNE RELATED DISEASES

FIELD OF THE INVENTION

The present invention relates to compositions and methods useful for the diagnosis and treatment of immune related diseases.

BACKGROUND OF THE INVENTION

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases, non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen -MHC complex on an antigen presenting cell. Helper T cells also secrete a variety of cytokines, i.e., lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)—CD28 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

In addition to the signals mediated through CD28 [Carreno et al., (2002) *Annu Rev Immunol* 20: 29-53], the molecule SLAM is also able to provide the second signal for co-stimulation of T cells necessary for proliferation [Aversa et al., (1997) *J Immunol* 158(9): 4036-4044, Aversa et al., (1997) *Immunol Cell Biol* 75(2): 202-205]. SLAM is a member of the family of molecules that contain extracelluar Ig-like repeats and also contain a SAP intracellular binding site characterized by the motif TxYxxV/I. Tyrosine phosphorylation of this motif greatly increases the binding of SAP with SLAM. As SAP is associated with X-linked lymphoproliferative disease, a greater understanding of the SAP/SLAM interaction may lead to further insights into treatment of this disease [Howie et al, (2002) *Blood* 99(3): 957-965, Latour et al., 2001, *Nat Immuno* 2(8): 681-690, Morra et al. 2001 *J Biol Chem* 276 (39): 36809-36816, Nichols et al., 2001 Nat Immunol 2(8): 665-666].

SLAM has been implicated in Th1 cell response, suggesting that this molecule may play a role in inflammation and autoimmune diseases [Cocks et al., (1995) *Nature* 376 (6537): 260-263, Aversa et al., (1997) *Immunol Cell Bio* 75(2): 202-205]. SLAM and CD3 crosslinking on the surface of T cells induces proliferation of T cells and an increase in Interferon gamma (IFN-γ) production. The reasons above lead to the search and discovery of a new member of the SLAM family, PRO20080. It is shown herein, that PRO20080 has homology to SLAM, and like SLAM, has expression in B cells, T cells and memory T cells. PRO20080 is upregulated on activated T cells, exhibits homotypic binding, contains SAP binding motifs and interacts with SAP in T cells. PRO20080 plus CD3 co-stimulation induces the proliferation of T cells and increases the production and secretion of IFN-γ. Evidence is also shown for PRO20080 in the Th1 mediated delayed-type hypersensitivity response, thus making PRO20080 a potential target for treatement of inflammation and Th1 mediated autoimmune diseases.

SUMMARY OF THE INVENTION

A. Embodiments

The present invention concerns compositions and methods useful for the diagnosis and treatment of immune related disease in mammals, including humans. The present invention is based on the identification of PRO20080 (including agonist and antagonist antibodies) which either stimulate or inhibit the immune response in mammals. Immune related diseases can be treated by suppressing or enhancing the immune response. Molecules that enhance the immune response stimulate or potentiate the immune response to an antigen. Molecules which stimulate the immune response can be used therapeutically where enhancement of the immune response would be beneficial. Alternatively, molecules that suppress the immune response attenuate or reduce the immune response to an antigen (e.g., neutralizing antibodies) can be used therapeutically where attenuation of the immune response would be beneficial (e.g., inflammation). Accordingly, the PRO20080 polypeptides, agonists and antagonists thereof are also useful to prepare medicines and medicaments for the treatment of immune-related and inflammatory diseases. In a specific aspect, such medicines and medicaments comprise a therapeutically effective amount of a PRO20080 polypeptide, agonist or antagonist thereof with a pharmaceutically acceptable carrier. Preferably, the admixture is sterile.

In a further embodiment, the invention concerns a method of identifying agonists or antagonists to a PRO20080 polypeptide which comprises contacting the PRO20080 polypeptide with a candidate molecule and monitoring a biological activity mediated by said PRO20080 polypeptide. Preferably, the PRO20080 polypeptide is a native sequence PRO20080 polypeptide. In a specific aspect, the PRO20080 agonist or antagonist is an anti-PRO20080 antibody.

In another embodiment, the invention concerns a composition of matter comprising a PRO20080 polypeptide or an agonist or antagonist antibody which binds the polypeptide in admixture with a carrier or excipient. In one aspect, the composition comprises a therapeutically effective amount of the polypeptide or antibody. In another aspect, when the composition comprises an immune stimulating molecule, the composition is useful for: (a) stimulating or enhancing an immune response in a mammal in need thereof, (b) increasing the proliferation of T-lymphocytes in a mammal in need thereof in response to an antigen, (c) stimulating the activity of T-lymphocytes (d) production of INF-γ. In another aspect, the composition comprises a further active ingredient, which may, for example, be a further antibody or a cytotoxic or chemotherapeutic agent. Preferably, the composition is sterile.

In another embodiment, the invention concerns a method of treating an immune related disorder in a mammal in need thereof, comprising administering to the mammal an effective amount of a PRO20080 polypeptide, an agonist thereof, or an antagonist thereto. In a preferred aspect, the immune related disorder is selected from the group consisting of: systemic lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In another embodiment, the invention provides an antibody which specifically binds to any of the above or below described polypeptides. Optionally, the antibody is a monoclonal antibody, humanized antibody, antibody fragment or single-chain antibody. In one aspect, the present invention concerns an isolated antibody which binds a PRO20080 polypeptide. In another aspect, the antibody mimics the activity of a PRO20080 polypeptide (an agonist antibody) or conversely the antibody inhibits or neutralizes the activity of a PRO20080 polypeptide (an antagonist antibody). In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a monoclonal antibody, a single-chain antibody, or an anti-idiotypic antibody.

In yet another embodiment, the present invention provides a composition comprising an anti-PRO20080 antibody in admixture with a pharmaceutically acceptable carrier. In one aspect, the composition comprises a therapeutically effective amount of the antibody. Preferably, the composition is sterile.

The composition may be administered in the form of a liquid pharmaceutical formulation, which may be preserved to achieve extended storage stability. Alternatively, the antibody is a monoclonal antibody, an antibody fragment, a humanized antibody, or a single-chain antibody.

In a further embodiment, the invention concerns an article of manufacture, comprising:

(a) a composition of matter comprising a PRO20080 polypeptide or agonist or antagonist thereof;

(b) a container containing said composition; and (c) a label affixed to said container, or a package insert included in said container referring to the use of said PRO20080 polypeptide or agonist or antagonist thereof in the treatment of an immune related disease. The composition may comprise a therapeutically effective amount of the PRO20080 polypeptide or the agonist or antagonist thereof.

In yet another embodiment, the present invention concerns a method of diagnosing an immune related disease in a mammal, comprising detecting the level of expression of a gene encoding a PRO20080 polypeptide (a) in a test sample of tissue cells obtained from the mammal, and (b) in a control sample of known normal tissue cells of the same cell type, wherein a higher or lower expression level in the test sample as compared to the control sample indicates the presence of immune related disease in the mammal from which the test tissue cells were obtained.

In another embodiment, the present invention concerns a method of diagnosing an immune disease in a mammal, comprising (a) contacting an anti-PRO20080 antibody with a test sample of tissue cells obtained from the mammal, and (b) detecting the formation of a complex between the antibody and a PRO20080 polypeptide, in the test sample; wherein the formation of said complex is indicative of the presence or absence of said disease. The detection may be qualitative or quantitative, and may be performed in comparison with monitoring the complex formation in a control sample of known normal tissue cells of the same cell type. A larger quantity of complexes formed in the test sample indicates the presence or absence of an immune disease in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality of the immune system.

In another embodiment, the invention provides a method for determining the presence of a PRO20080 polypeptide in a sample comprising exposing a test sample of cells suspected of containing the PRO20080 polypeptide to an anti-PRO20080 antibody and determining the binding of said antibody to said cell sample. In a specific aspect, the sample comprises a cell suspected of containing the PRO20080 polypeptide and the antibody binds to the cell. The antibody is preferably detectably labeled and/or bound to a solid support.

In another embodiment, the present invention concerns an immune-related disease diagnostic kit, comprising an anti-PRO20080 antibody and a carrier in suitable packaging. The kit preferably contains instructions for using the antibody to detect the presence of the PRO20080 polypeptide. Preferably the carrier is pharmaceutically acceptable.

In another embodiment, the present invention concerns a diagnostic kit, containing an anti-PRO20080 antibody in suitable packaging. The kit preferably contains instructions for using the antibody to detect the PRO20080 polypeptide.

In another embodiment, the invention provides a method of diagnosing an immune-related disease in a mammal which comprises detecting the presence or absence or a PRO20080 polypeptide in a test sample of tissue cells obtained from said mammal, wherein the presence or absence of the PRO20080 polypeptide in said test sample is indicative of the presence of an immune-related disease in said mammal.

In another embodiment, the present invention concerns a method for identifying an agonist of a PRO20080 polypeptide comprising:

(a) contacting cells and a test compound to be screened under conditions suitable for the induction of a cellular response normally induced by a PRO20080 polypeptide; and (b) determining the induction of said cellular response to determine if the test compound is an effective agonist, wherein the induction of said cellular response is indicative of said test compound being an effective agonist.

In another embodiment, the invention concerns a method for identifying a compound capable of inhibiting the activity of a PRO20080 polypeptide comprising contacting a candidate compound with a PRO20080 polypeptide under conditions and for a time sufficient to allow these two components to interact and determining whether the activity of the PRO20080 polypeptide is inhibited. In a specific aspect, either the candidate compound or the PRO20080 polypeptide is immobilized on a solid support. In another aspect, the non-immobilized component carries a detectable label. In a preferred aspect, this method comprises the steps of:

(a) contacting cells and a test compound to be screened in the presence of a PRO20080 polypeptide under conditions suitable for the induction of a cellular response normally induced by a PRO20080 polypeptide; and (b) determining the induction of said cellular response to determine if the test compound is an effective antagonist.

In another embodiment, the invention provides a method for identifying a compound that inhibits the expression of a PRO20080 polypeptide in cells that normally express the polypeptide, wherein the method comprises contacting the cells with a test compound and determining whether the expression of the PRO20080 polypeptide is inhibited. In a preferred aspect, this method comprises the steps of:

(a) contacting cells and a test compound to be screened under conditions suitable for allowing expression of the PRO20080 polypeptide; and (b) determining the inhibition of expression of said polypeptide.

In yet another embodiment, the present invention concerns a method for treating an immune-related disorder in a mammal that suffers therefrom comprising administering to the mammal a nucleic acid molecule that codes for either (a) a PRO20080 polypeptide, (b) an agonist of a PRO20080 polypeptide or (c) an antagonist of a PRO20080 polypeptide, wherein said agonist or antagonist may be an anti-PRO20080 antibody. In a preferred embodiment, the mammal is human. In another preferred embodiment, the nucleic acid is administered via ex vivo gene therapy. In a further preferred embodiment, the nucleic acid is comprised within a vector, more preferably an adenoviral, adeno-associated viral, lentiviral or retroviral vector.

In yet another aspect, the invention provides a recombinant viral particle comprising a viral vector consisting essentially of a promoter, nucleic acid encoding (a) a PRO20080 polypeptide, (b) an agonist polypeptide of a PRO20080 polypeptide, or (c) an antagonist polypeptide of a PRO20080 polypeptide, and a signal sequence for cellular secretion of the polypeptide, wherein the viral vector is in association with viral structural proteins. Preferably, the signal sequence is from a mammal, such as from a native PRO20080 polypeptide.

In a still further embodiment, the invention concerns an ex vivo producer cell comprising a nucleic acid construct that expresses retroviral structural proteins and also comprises a retroviral vector consisting essentially of a promoter, nucleic acid encoding (a) a PRO20080 polypeptide, (b) an agonist polypeptide of a PRO20080 polypeptide or (c) an antagonist polypeptide of a PRO20080 polypeptide, and a signal sequence for cellular secretion of the polypeptide, wherein said producer cell packages the retroviral vector in association with the structural proteins to produce recombinant retroviral particles.

In a still further embodiment, the invention provides a method of increasing the activity of T-lymphocytes in a mammal comprising administering to said mammal (a) a PRO20080 polypeptide, (b) an agonist of a PRO20080 polypeptide, wherein the activity of T-lymphocytes in the mammal is increased.

In a still further embodiment, the invention provides a method of decreasing the activity of T-lymphocytes in a mammal comprising administering to said mammal an antagonist of a PRO20080 polypeptide, wherein the activity of T-lymphocytes in the mammal is decreased.

In a still further embodiment, the invention provides a method of increasing the proliferation of T-lymphocytes in a mammal comprising administering to said mammal (a) a PRO20080 polypeptide, (b) an agonist of a PRO20080 polypeptide, wherein the proliferation of T-lymphocytes in the mammal is increased.

In a still further embodiment, the invention provides a method of decreasing the proliferation of T-lymphocytes in a mammal comprising administering to said mammal an antagonist of a PRO20080 polypeptide, wherein the proliferation of T-lymphocytes in the mammal is decreased.

In a still further embodiment, the invention provides a method of decreasing the Th1 mediated delayed type hypersensitive response in a mammal comprising administering to said mammal an antagonist of a PRO20080 polypeptide, wherein the Th I mediated delayed type hypersensitive response is decreased.

In a still further embodiment, the invention provides a method of inhibiting the inflammatory immune response, said method comprising contacting a T cell line containing a reporter construct with a PRO20080 antagonist thereof, wherein said inflammatory immune response is inhibited and measured.

B. Additional Embodiments

In other embodiments of the present invention, the invention provides vectors comprising DNA encoding any of the herein described polypeptides. Host cell comprising any such vector are also provided. By way of example, the host cells may be CHO cells, E. coli, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a PRO20080 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO20080 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO20080 polypeptide cDNA as disclosed herein, the coding sequence of a PRO20080 polypeptide lacking the signal peptide as disclosed herein, the coding sequence of an extracellular domain of a transmembrane PRO20080 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO20080 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO20080 polypeptides are contemplated.

Another embodiment is directed to fragments of a PRO20080 polypeptide coding sequence, or the complement thereof, that may find use as, for example, hybridization probes, for encoding fragments of a PRO20080 polypeptide that may optionally encode a polypeptide comprising a binding site for an anti-PRO20080 antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO20080 polypeptide-encoding nucleotide sequence may be determined in a routine manner by aligning the PRO20080 polypeptide-encoding nucleotide sequence with other known nucleotide sequences using any of a number of well known sequence alignment programs and determining which PRO20080 polypeptide-encoding nucleotide sequence fragment(s) are novel. All of such PRO20080 polypeptide-encoding nucleotide sequences are contemplated herein. Also contemplated are the PRO20080 polypeptide fragments encoded by these nucleotide molecule fragments, preferably those PRO20080 polypeptide fragments that comprise a binding site for an anti-PRO20080 antibody.

In another embodiment, the invention provides isolated PRO20080 polypeptide encoded by any of the isolated nucleic acid sequences herein above identified.

In a certain aspect, the invention concerns an isolated PRO20080 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO20080 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO20080 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO20080 polypeptide without the N-terminal signal sequence and/or the initiating methionine and is encoded by a nucleotide sequence that encodes such an amino acid sequence as herein before described. Processes for producing the same are also herein described, wherein those processes comprise culturing a host cell comprising a vector which comprises the appropriate encoding nucleic acid molecule under conditions suitable for expression of the PRO20080 polypeptide and recovering the PRO20080 polypeptide from the cell culture.

Another aspect the invention provides an isolated PRO20080 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO20080 polypeptide and recovering the PRO20080 polypeptide from the cell culture.

In yet another embodiment, the invention concerns agonists and antagonists of a native PRO20080 polypeptide as defined herein. In a particular embodiment, the agonist or antagonist is an anti-PRO20080 antibody or a small molecule.

In a further embodiment, the invention concerns a method of identifying agonists or antagonists to a PRO20080 polypeptide which comprise contacting the PRO20080 polypeptide with a candidate molecule and monitoring a biological activity mediated by said PRO20080 polypeptide. Preferably, the PRO20080 polypeptide is a native PRO20080 polypeptide.

In a still further embodiment, the invention concerns a composition of matter comprising a PRO20080 polypeptide, or an agonist or antagonist of a PRO20080 polypeptide as herein described, or an anti-PRO20080 antibody, in combination with a carrier. Optionally, the carrier is a pharmaceutically acceptable carrier.

Another embodiment of the present invention is directed to the use of a PRO20080 polypeptide, or an agonist or antagonist thereof as herein before described, or an anti-PRO20080 antibody, for the preparation of a medicament useful in the treatment of a condition which is responsive to the PRO20080 polypeptide, an agonist or antagonist thereof or an anti-PRO20080 antibody.

BRIEF DESCRIPTION OF THE DRAWINGS

FIG. 1 shows a nucleotide sequence (SEQ ID NO:1) of a native sequence PRO20080 cDNA, wherein SEQ ID NO:1 is a clone designated herein as "DNA161000-2896".

FIG. 2 shows the amino acid sequence (SEQ ID NO:2) derived from the coding sequence of SEQ ID NO:1 shown in FIG. 1.

FIG. 4 shows the expression of PRO20080 in a panel of cell lines.

FIG. 9a shows the phosphorylated state of PRO20080 and its association with SAP.

FIG. 9b shows a time course of phosphorylation of PRO20080 upon co-stimulation treatment and addition of a cross linking antibody.

FIG. 9c shows the phosphorylated state of PRO20080 and its association with SAP upon co-stimulation.

DETAILED DESCRIPTION OF THE PREFERRED EMBODIMENTS

I. Definitions

Figure 3:
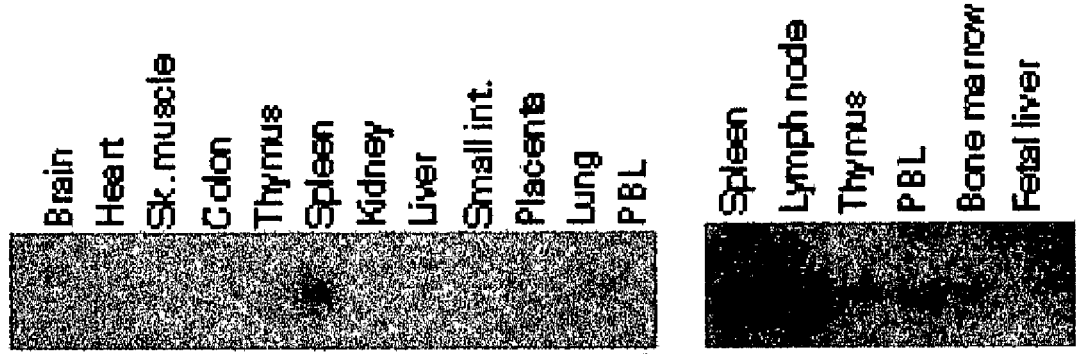
FIG. 3 shows a Northern Blot analysis of the expression of PRO20080.

The terms "PRO20080 polypeptide" and "PRO20080" as used herein encompass native sequence polypeptides and polypeptide variants (which are further defined herein). The PRO20080 polypeptides described herein may be isolated from a variety of sources, such as from human tissue types or from another source, or prepared by recombinant or synthetic methods. The term "PRO20080 polypeptide" refers to each individual PRO20080/number polypeptide disclosed herein. All disclosures in this specification which refer to the "PRO20080 polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO20080 polypeptide" also includes variants of the PRO20080 polypeptides disclosed herein.

A "native sequence PRO20080 polypeptide" comprises a polypeptide having the same amino acid sequence as the corresponding PRO20080 polypeptide derived from nature. Such native sequence PRO20080 polypeptides can be isolated from nature or can be produced by recombinant or synthetic means. The term "native sequence PRO20080 polypeptide" specifically encompasses naturally-occurring truncated or secreted forms of the specific PRO20080 polypeptide (e.g., an extracellular domain sequence), natu-rally-occurring variant forms (e.g., alternatively spliced forms) and naturally-occurring allelic variants of the polypeptide. In various embodiments of the invention, the native sequence PRO20080 polypeptides disclosed herein are mature or full-length native sequence polypeptides comprising the full-length amino acids sequences shown in the accompanying figures. Start and stop codons are shown in bold font and underlined in the figures. However, while the PRO20080 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO20080 polypeptides.

The PRO20080 polypeptide "extracellular domain" or "ECD" refers to a form of the PRO20080 polypeptide which is essentially free of the transmembrane and cytoplasmic domains. Ordinarily, a PRO20080 polypeptide ECD will have less than 1% of such transmembrane and/or cytoplasmic domains and preferably, will have less than 0.5% of such domains. It will be understood that any transmembrane domains identified for the PRO20080 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO20080 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO20080 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6(1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO20080 polypeptide variant" means an active PRO20080 polypeptide as defined above or below having at least about 80% amino acid sequence identity with a full-length native sequence PRO20080 polypeptide sequence as disclosed herein, a PRO20080 polypeptide sequence lacking the signal peptide as disclosed herein, an extracellular domain of a PRO20080 polypeptide, with or without the signal peptide, as disclosed herein or any other fragment of a full-length PRO20080 polypeptide sequence as disclosed herein. Such PRO20080 polypeptide variants include, for instance, PRO20080 polypeptides wherein one or more amino acid residues are added, or deleted, at the N- or C-terminus of the full-length native amino acid sequence. Ordinarily, a PRO20080 polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO20080 polypeptide sequence as disclosed herein, a PRO20080 polypeptide sequence lacking the signal peptide as disclosed herein, an extracellular domain of a PRO20080 polypeptide, with or without the signal peptide, as disclosed herein or any other specifically defined fragment of a full-length PRO20080 polypeptide sequence as disclosed herein. Ordinarily, PRO20080 variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO20080 polypeptide sequences identified herein is defined as the percentage of amino acid residues in a candidate sequence that are identical with the amino acid residues in the specific PRO20080 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO20080", wherein "PRO20080" represents the amino acid sequence of a hypothetical PRO20080 polypeptide of interest, "Comparison Protein" represents the amino acid sequence of a polypeptide against which the "PRO20080" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO20080 polypeptide of interest having a sequence derived from the native PRO20080 polypeptide and the comparison amino acid sequence of interest (i.e., the sequence against which the PRO20080 polypeptide of interest is being compared which may be a PRO20080 variant polypeptide) as determined by WU-BLAST-2 by (b) the total number of amino acid residues of the PRO20080 polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO20080 polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO20080 variant polynucleotide" or "PRO20080 variant nucleic acid sequence" means a nucleic acid molecule which encodes an active PRO20080 polypeptide as defined below and which has at least about 80% nucleic acid sequence identity with a nucleotide acid sequence encoding a full-length native sequence PRO20080 polypeptide sequence as disclosed herein, a full-length native sequence PRO20080 polypeptide sequence lacking the signal peptide as disclosed herein, an extracellular domain of a PRO20080 polypeptide, with or without the signal peptide, as disclosed herein or any other fragment of a full-length PRO20080 polypeptide sequence as disclosed herein. Ordinarily, a PRO20080 variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO20080 polypeptide sequence as disclosed herein, a full-length native sequence PRO20080 polypeptide sequence lacking the signal peptide as disclosed herein, an extracellular domain of a PRO20080 polypeptide, with or without the signal sequence, as disclosed herein or any other fragment of a full-length PRO20080 polypeptide sequence as disclosed herein. Variants do not encompass the native nucleotide sequence.

Ordinarily, PRO20080 variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO20080-encoding nucleic acid sequences identified herein is defined as the percentage of nucleotides in a candidate sequence that are identical with the nucleotides in the PRO20080 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNAS-TAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO20080-DNA", wherein "PRO20080-DNA" represents a hypothetical PRO20080-encoding nucleic acid sequence of interest, "Comparison DNA" represents the nucleotide sequence of a nucleic acid molecule against which the "PRO20080-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO20080 polypeptide-encoding nucleic acid molecule of interest having a sequence derived from the native sequence PRO20080 polypeptide-encoding nucleic acid and the comparison nucleic acid molecule of interest (i.e., the sequence against which the PRO20080 polypeptide-encoding nucleic acid molecule of interest is being compared which may be a variant PRO20080 polynucleotide) as determined by WU-BLAST-2 by (b) the total number of nucleotides of the PRO20080 polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO20080 polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO20080 variant polynucleotides are nucleic acid molecules that encode an active PRO20080 polypeptide and which are capable of hybridizing, preferably under stringent hybridization and wash conditions, to nucleotide sequences encoding a full-length PRO20080 polypeptide as disclosed herein. PRO20080 variant polypeptides may be those that are encoded by a PRO20080 variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO20080 polypeptide natural environment will not be present. Ordinarily, however, isolated polypeptide will be prepared by at least one purification step.

An "isolated" PRO20080 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO20080 monoclonal antibodies (including agonist, antagonist, and neutralizing antibodies), anti-PRO20080 antibody compositions with polyepitopic specificity, single chain anti-PRO20080 antibodies, and fragments of anti-PRO20080 antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO20080 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO20080 polypeptide which retain a biological and/or an immunological activity of native or naturally-occurring PRO20080, wherein "biological" activity refers to a biological function (either inhibitory or stimulatory) caused by a native or naturally-occurring PRO20080 other than the ability to induce the production of an antibody against an antigenic epitope possessed by a native or naturally-occurring PRO20080 and an "immunological" activity refers to the ability to induce the production of an antibody against an antigenic epitope possessed by a native or naturally-occurring PRO20080.

The term "antagonist" is used in the broadest sense, and includes any molecule that partially or fully blocks, inhibits, or neutralizes a biological activity of a native PRO20080 polypeptide disclosed herein. In a similar manner, the term "agonist" is used in the broadest sense and includes any molecule that mimics a biological activity of a native PRO20080 polypeptide disclosed herein. Suitable agonist or antagonist molecules specifically include agonist or antagonist antibodies or antibody fragments, fragments or amino acid sequence variants of native PRO20080 polypeptides, peptides, antisense oligonucleotides, small organic molecules, etc. Methods for identifying agonists or antagonists of a PRO20080 polypeptide may comprise contacting a PRO20080 polypeptide with a candidate agonist or antagonist molecule and measuring a detectable change in one or more biological activities normally associated with the PRO20080 polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO20080 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft -versus-host-disease. Infectious diseases including viral diseases such as AIDS (HIV infection), hepatitis A, B, C, D, and E, herpes, etc., bacterial infections, fungal infections, protozoal infections and parasitic infections.

The term "effective amount" is a concentration or amount of a PRO20080 polypeptide and/or agonist/antagonist which results in achieving a particular stated purpose. An "effective amount" of a PRO20080 polypeptide or agonist or antagonist thereof may be determined empirically. Furthermore, a "therapeutically effective amount" is a concentration or amount of a PRO20080 polypeptide and/or agonist/antagonist which is effective for achieving a stated therapeutic effect. This amount may also be determined empirically.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

As used herein, the term "inflammatory cells" designates cells that enhance the inflammatory response such as mononuclear cells, eosinophils, macrophages, and polymorphonuclear neutrophils (PMN).

As used herein, the term "delayed type hypersensitivity" or "DTH" is an immune reaction caused by an antigen and is mediated by the cellular component of the immune system, specifically, memory T cells. The hallmark DTH response is is induration, swelling, edema and monocytic infiltration into the site of the lesion within 24 to 72 hours. DTH has been classified at Type IV hypersensitivity by Coombs and Gell [Gell et al., (1968) *Clinical Aspects in Immunology*, Blackwell, Oxford]

Table 1

```
/*
 *
 * C-C increased from 12 to 15
 * Z is average of EQ
 * B is average of ND
 * match with stop is _M; stop-stop = 0; J (joker) match = 0
 */
define   _M      -8       /* value of a match with a stop */ int       _day[26][26] = {
/*        A B C D E F G H I J K L M N O P Q R S T U V W X Y Z */
/* A */   { 2, 0,-2, 0, 0,-4, 1,-1,-1, 0,-1,-2,-1, 0,_M, 1, 0,-2, 1, 1, 0, 0,-6, 0,-3, 0},
/* B */   { 0, 3,-4, 3, 2,-5, 0, 1,-2, 0, 0,-3,-2, 2,_M,-1, 1, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M, 0,_M,_M,_M,_M,_M,_M,_M, M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3, 2,-2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define   MAXJMP    16      /* max jumps in a diag */
define   MAXGAP    24      /* don't continue to penalize gaps larger than this */
#define   JMPS      1024    /* max jmps in an path */
define   MX        4       /* save if there's at least MX-1 bases since last jmp */ define   DMAT      3       /* value of matching bases */
define   DMIS      0       /* penalty for mismatched bases */
#define   DINS0     8       /* penalty for a gap */
#define   DINS1     1       /* penalty per base */
#define   PINS0     8       /* penalty for a gap */
define   PINS1     4       /* penalty per residue */ struct jmp {
          short           n[MAXJMP];        /* size of jmp (neg for dely) */
          unsigned short  x[MAXJMP];        /* base no. of jmp in seq x */
};                                          /* limits seq to 2^16 -1 */ struct diag {
          int             score;            /* score at last jmp */
          long            offset;           /* offset of prev block */
          short           ijmp;             /* current jmp index */
          struct jmp      jp;               /* list of jmps */
};

struct path {
          int             spc;              /* number of leading spaces */
          short           n[JMPS];/* size of jmp (gap) */
          int             x[JMPS];/* loc of jmp (last elem before gap) */
};

char            *ofile;           /* output file name */
          char            *namex[2];        /* seq names: getseqs() */
          char            *prog;            /* prog name for err msgs */
          char            *seqx[2];         /* seqs: getseqs() */
          int             dmax;             /* best diag: nw() */
          int             dmax0;            /* final diag */
          int             dna;              /* set if dna: main() */
          int             endgaps;          /* set if penalizing end gaps */
          int             gapx, gapy;       /* total gaps in seqs */
          int             len0, len1;       /* seq lens */
          int             ngapx, ngapy;     /* total size of gaps */
          int             smax;             /* max score: nw() */
          int             *xbm;             /* bitmap for matching */
          long            offset;           /* current offset in jmp file */
          struct diag     *dx;              /* holds diagonals */
          struct path     pp[2];            /* holds path for seqs */ char            *calloc(), *malloc(), *index(), *strcpy();
          char            *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 *   The program may create a tmp file in /tmp to hold info about traceback.
 *   Original version developed under BSD 4.3 on a vax 8650
 */
include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                                main
        int     ac;
        char    *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();                   /* fill in the matrix, get the possible jmps */
        readjmps();             /* get the actual jmps */
        print();                /* print stats, alignment */ cleanup(0);             /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                                    nw
{
        char            *px, *py;           /* seqs and ptrs */
        int             *ndely, *dely;      /* keep track of dely */
        int             ndelx, delx;        /* keep track of delx */
        int             *tmp;               /* for swapping row0, row1 */
        int             mis;                /* score for each type */
        int             ins0, ins1;         /* insertion penalties */
        register        id;                 /* diagonal index */
        register        ij;                 /* jmp index */
        register        *col0, *col1;       /* score for curr, last row */
        register        xx, yy;             /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;        /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 1 (cont')

...nw

```
                        id = xx - yy + len1 - 1;
                        if (mis >= delx && mis >= dely[yy])
                                col1[yy] = mis;
                        else if (delx >= dely[yy]) {
                                col1[yy] = delx;
                                ij = dx[id].ijmp;
                                if (dx[id].jp.n[0] && (!dna || (ndelx >= MAXJMP
                                        && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = ndelx;
                                dx[id].jp.x[ij] = xx;
                                dx[id].score = delx;
                        }
                        else {
                                col1[yy] = dely[yy];
                                ij = dx[id].ijmp;
                if (dx[id].jp.n[0] && (!dna || (ndely[yy] >= MAXJMP
                                        && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = -ndely[yy];
                                dx[id].jp.x[ij] = xx;
                                dx[id].score = dely[yy];
                        }
                        if (xx == len0 && yy < len1) {
                                /* last col
                                */
                                if (endgaps)
                                        col1[yy] -= ins0+ins1*(len1-yy);
                                if (col1[yy] > smax) {
                                        smax = col1[yy];
                                        dmax = id;
                                }
                        }
                }
                if (endgaps && xx < len0)
                        col1[yy-1] -= ins0+ins1*(len0-xx);
                if (col1[yy-1] > smax) {
                        smax = col1[yy-1];
                        dmax = id;
                }
        }
        tmp = col0; col0 = col1; col1 = tmp;
}
(void) free((char *)ndely);
(void) free((char *)dely);
(void) free((char *)col0);
(void) free((char *)col1);                              }
```

Table 1 (cont')

```
/*
 *
 * print() -- only routine visible outside this module
 *
 * static:
 * getmat() -- trace back best path, count matches: print()
 * pr_align() -- print alignment of described in array p[ ]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC      3
#define P_LINE   256        /* maximum output line */
define P_SPC    3          /* space between name or num and seq */ extern   _day[26][26];
int      olen;              /* set output line length */
FILE     *fx;               /* output file */ print()
{
        int     lx, ly, firstgap, lastgap;    /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
``` print

Table 1 (cont')

```
/*
 * trace back the best path, count matches
 */
static
getmat(lx, ly, firstgap, lastgap)
        int     lx, ly;                 /* "core" (minus endgaps) */
        int     firstgap, lastgap;      /* leading trailing overlap */
{
        int     nm, i0, i1, siz0, siz1;
        char    outx[32];
        double  pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
``` getmat

Table 1 (cont')

```
                fprintf(fx, "<gaps in first sequence: %d", gapx);                        ...getmat
        if (gapx) {
                        (void) sprintf(outx, " (%d %s%s)",
                                ngapx, (dna)? "base":"residue", (ngapx == 1)? "":"s");
                        fprintf(fx,"%s", outx);

fprintf(fx, ", gaps in second sequence: %d", gapy);
        if (gapy) {
                        (void) sprintf(outx, " (%d %s%s)",
                                ngapy, (dna)? "base":"residue", (ngapy == 1)? "":"s");
                        fprintf(fx,"%s", outx);

}
        if (dna)
                        fprintf(fx,
                        "\n<score: %d (match = %d, mismatch = %d, gap penalty = %d + %d per base)\n",
                        smax, DMAT, DMIS, DINS0, DINS1);
                else
                        fprintf(fx,
                        "\n<score: %d (Dayhoff PAM 250 matrix, gap penalty = %d + %d per residue)\n",
                        smax, PINS0, PINS1);
        if (endgaps)
                        fprintf(fx,
                        "<endgaps penalized. left endgap: %d %s%s, right endgap: %d %s%s\n",
                        firstgap, (dna)? "base" : "residue", (firstgap == 1)? "" : "s",
                        lastgap, (dna)? "base" : "residue", (lastgap == 1)? "" : "s");
                else
                        fprintf(fx, "<endgaps not penalized\n");
}
        static          nm;              /* matches in core -- for checking */
        static          lmax;            /* lengths of stripped file names */
        static          ij[2];           /* jmp index for a path */
        static          nc[2];           /* number at start of current line */
        static          ni[2];           /* current elem number -- for gapping */
        static          siz[2];
        static char     *ps[2];          /* ptr to current element */
        static char     *po[2];          /* ptr to next output char slot */
        static char     out[2][P_LINE];  /* output line */
        static char     star[P_LINE];    /* set by stars() */

/*
        * print alignment of described in struct path pp[ ]
        */
        static
        pr_align()                                                                       pr_align
        {
                int             nn;     /* char count */
                int             more;
                register        i;

for (i = 0, lmax = 0; i < 2; i++) {
                        nn = stripname(namex[i]);
                        if (nn > lmax)
                                lmax = nn;

nc[i] = 1;
                        ni[i] = 1;
                        siz[i] = ij[i] = 0;
                        ps[i] = seqx[i];
                        po[i] = out[i];                          }
```

Table 1 (cont')

```
        for (nn = nm = 0, more = 1; more; ) {                          ...pr_align
                for (i = more = 0; i < 2; i++) {
                        /*
                         * do we have more of this sequence?
                         */
                        if (!*ps[i])
                                continue;
                        more++;

if (pp[i].spc) {        /* leading space */
                                *po[i]++ = ' ';
                                pp[i].spc--;
                        }
                        else if (siz[i]) {      /* in a gap */
                                *po[i]++ = '-';
                                siz[i]--;
                        }
                        else {                  /* we're putting a seq element
                                                 */
                                *po[i] = *ps[i];
                                if (islower(*ps[i]))
                                        *ps[i] = toupper(*ps[i]);
                                po[i]++;
                                ps[i]++;

/*
                                 * are we at next gap for this seq?
                                 */
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];
                                }
                                ni[i]++;
                        }
                }
                if (++nn == olen || !more && nn) {
                        dumpblock();
                        for (i = 0; i < 2; i++)
                                po[i] = out[i];
                        nn = 0,
                }
        }
}

/*
 * dump a block of lines, including numbers, stars: pr_align()
 */
static
dumpblock()                                                             dumpblock
{
        register i;
        for (i = 0; i < 2; i++)
                *po[i]-- = '\0';
```

Table 1 (cont')

...dumpblock

```
                (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars();
                        putline(i);
                        if (i == 0 && *out[1])
                                fprintf(fx, star);
                        if (i == 1)
                                nums(i);
                }
        }
}

/*
 * put out a number line: dumpblock()
 */
static
nums(ix)
        int     ix;     /* index in out[ ] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
 * put out a line (name, [num], seq, [num]): dumpblock()
 */
static
putline(ix)
        int     ix;                             {
``` nums putline

Table 1 (cont')

...putline

```
        int         i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[ ] is current element (from 1)
         * nc[ ] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int         i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
``` stars

Table 1 (cont')

```
/*
 * strip path or prefix from pn, return len: pr_align()
 */
static
stripname(pn)
        char       *pn;      /* file name (may be path) */
{
        register char    *px, *py;

py = 0;
        for (px = pn; *px; px++)
                if (*px == '/')
                        py = px + 1;
        if (py)
                (void) strcpy(pn, py);
        return(strlen(pn));

}
``` stripname

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";     /* tmp file for jmps */
        FILE    *fj;

int     cleanup();                      /* cleanup tmp file */
        long    lseek();

/*
 * remove any tmp file if we blow
 */
cleanup(i)                                                                          cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                                   getseq
        char    *file;  /* file name */
        int     *len;   /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
                py = pseq + 4;
                *len = tlen;
                rewind(fp);

while (fgets(line, 1024, fp)) {
                        if (*line == ';' || *line == '<' || *line == '>')
                                continue;
                        for (px = line; *px != '\n', px++) {
                                if (isupper(*px))
                                        *py++ = *px;
                                else if (islower(*px))
                                        *py++ = toupper(*px);
                                if (index("ATGCU",*(py-1)))
                                        natgc++;
                        }
                }
                *py++ = '\0';
                *py = '\0';
                (void) fclose(fp);
                dna = natgc > (tlen/3);
                return(pseq+4);
        }
        char    *
        g_calloc(msg, nx, sz)
                char    *msg;           /* program, calling routine */
                int     nx, sz;         /* number and size of elements */
        {
                char    *px, *calloc();

if ((px = calloc((unsigned)nx, (unsigned)sz)) == 0) {
                        if (*msg) {
                                fprintf(stderr, "%s: g_calloc() failed %s (n=%d, sz=%d)\n", prog, msg, nx, sz);
                                exit(1);
                        }
                }
                return(px);
        }

/*
        * get final jmps from dx[ ] or tmp file, set pp[ ], reset dmax: main()
        */
        readjmps()
        {
                int     fd = -1;
                int     siz, i0, i1;
                register i, j, xx;

if (fj) {
                        (void) fclose(fj);
                        if ((fd = open(jname, O_RDONLY, 0)) < 0) {
                                fprintf(stderr, "%s: can't open() %s\n", prog, jname);
                                cleanup(1);
                        }
                }
                for (i = i0 = i1 = 0, dmax0 = dmax, xx = len0; ; i++) {
                        while (1) {
                                for (j = dx[dmax].ijmp; j >= 0 && dx[dmax].jp.x[j] >= xx; j--)
                                        ;
``` g_calloc readjmps

Table 1 (cont')

...readjmps

```
            if (j < 0 && dx[dmax].offset && fj) {
                    (void) lseek(fd, dx[dmax].offset, 0);
                    (void) read(fd, (char *)&dx[dmax].jp, sizeof(struct jmp));
                    (void) read(fd, (char *)&dx[dmax].offset, sizeof(dx[dmax].offset));
                    dx[dmax].ijmp = MAXJMP-1;
            }
            else
                    break;
    }
    if (i >= JMPS) {
            fprintf(stderr, "%s: too many gaps in alignment\n", prog);
            cleanup(1);
    }
    if (j >= 0) {
            siz = dx[dmax].jp.n[j];
            xx = dx[dmax].jp.x[j];
            dmax += siz;
            if (siz < 0) {                    /* gap in second seq */
                    pp[1].n[i1] = -siz;
                    xx += siz;
                    /* id = xx - yy + len1 - 1
                    */
                    pp[1].x[i1] = xx - dmax + len1 - 1;
                    gapy++;
                    ngapy -= siz;
    /* ignore MAXGAP when doing endgaps */
                    siz = (-siz < MAXGAP || endgaps)? -siz : MAXGAP;
                    i1++;
            }
            else if (siz > 0) {    /* gap in first seq */
                    pp[0].n[i0] = siz;
                    pp[0].x[i0] = xx;
                    gapx++;
                    ngapx += siz;
    /* ignore MAXGAP when doing endgaps */
                    siz = (siz < MAXGAP || endgaps)? siz : MAXGAP;
                    i0++;
            }
    }
    else
            break;
}
/* reverse the order of jmps
*/
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
}
```

42

Table 1 (cont')

```
/*
 * write a filled jmp struct offset of the prev one (if any): nw()
 */
writejmps(ix)                                                                writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO20080 | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO20080 polypeptide) = 5 divided by 15 = 33.3%

TABLE 3

| | | |
|---|---|---|
| PRO20080 | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO20080 polypeptide) = 5 divided by 10 = 50%

TABLE 4

| | | |
|---|---|---|
| PRO20080-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO20080-DNA nucleic acid sequence) = 6 divided by 14 = 42.9%

TABLE 5

| | | |
|---|---|---|
| PRO20080-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO20080-DNA nucleic acid sequence) = 4 divided by 12 = 33.3%

II. Compositions and Methods of the Invention

A. Full-Length PRO20080 Polypeptides

The present invention provides newly identified and isolated nucleotide sequences encoding polypeptides referred to in the present application as PRO20080 polypeptides. In particular, cDNAs encoding various PRO20080 polypeptides have been identified and isolated, as disclosed in further detail in the Examples below. It is noted that proteins produced in separate expression rounds may be given different PRO20080 numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO20080, will be referred to as "PRO20080/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO20080 polypeptides and encoding nucleic acids described herein, Applicants have identified what is believed to be the reading frame best identifiable with the sequence information available at the time.

B. PRO20080 Polypeptide Variants

In addition to the full-length native sequence PRO20080 polypeptides described herein, it is contemplated that PRO20080 variants can be prepared. PRO20080 variants can be prepared by introducing appropriate nucleotide changes into the PRO20080 DNA, and/or by synthesis of the desired PRO20080 polypeptide. Those skilled in the art will appreciate that amino acid changes may alter post-translational processes of the PRO20080, such as changing the number or position of glycosylation sites or altering the membrane anchoring characteristics.

Variations in the native full-length sequence PRO20080 or in various domains of the PRO20080 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO20080 that results in a change in the amino acid sequence of the PRO20080 as compared with the native sequence PRO20080. Optionally, the variation is by substitution of at least one amino acid with any other amino acid in one or more of the domains of the PRO20080. Guidance in determining which amino acid residue may be inserted, substituted or deleted without adversely affecting the desired activity may be found by comparing the sequence of the PRO20080 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO20080 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO20080 polypeptide.

PRO20080 fragments may be prepared by any of a number of conventional techniques. Desired peptide fragments may be chemically synthesized. An alternative approach involves generating PRO20080 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO20080 polypeptide fragments share at least one biological and/or immunological activity with the native PRO20080 polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO20080 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO20080 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO20080

Covalent modifications of PRO20080 are included within the scope of this invention. One type of covalent modification includes reacting targeted amino acid residues of a PRO20080 polypeptide with an organic derivatizing agent that is capable of reacting with selected side chains or the N- or C-terminal residues of the PRO20080. Derivatization with bifunctional agents is useful, for instance, for crosslinking PRO20080 to a water-insoluble support matrix or surface for use in the method for purifying anti-PRO20080 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79-86 (1983)], acetylation of the N-terminal amine, and amidation of any C-terminal carboxyl group.

Another type of covalent modification of the PRO20080 polypeptide included within the scope of this invention comprises altering the native glycosylation pattern of the polypeptide. "Altering the native glycosylation pattern" is intended for purposes herein to mean deleting one or more carbohydrate moieties found in native sequence PRO20080 (either by removing the underlying glycosylation site or by deleting the glycosylation by chemical and/or enzymatic means), and/or adding one or more glycosylation sites that are not present in the native sequence PRO20080. In addition, the phrase includes qualitative changes in the glycosylation of the native proteins, involving a change in the nature and proportions of the various carbohydrate moieties present.

Addition of glycosylation sites to the PRO20080 polypeptide may be accomplished by altering the amino acid sequence. The alteration may be made, for example, by the addition of, or substitution by, one or more serine or threonine residues to the native sequence PRO20080 (for O-linked glycosylation sites). The PRO20080 amino acid sequence may optionally be altered through changes at the DNA level, particularly by mutating the DNA encoding the PRO20080 polypeptide at preselected bases such that codons are generated that will translate into the desired amino acids.

Another means of increasing the number of carbohydrate moieties on the PRO20080 polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259-306 (1981).

Removal of carbohydrate moieties present on the PRO20080 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO20080 comprises linking the PRO20080 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO20080 of the present invention may also be modified in a way to form a chimeric molecule comprising PRO20080 fused to another, heterologous polypeptide or amino acid sequence.

In one embodiment, such a chimeric molecule comprises a fusion of the PRO20080 with a tag polypeptide which provides an epitope to which an anti-tag antibody can selectively bind. The epitope tag is generally placed at the amino- or carboxyl-terminus of the PRO20080. The presence of such epitope-tagged forms of the PRO20080 can be detected using an antibody against the tag polypeptide. Also, provision of the epitope tag enables the PRO20080 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an alpha-tubulin epitope peptide [Skinner et al., *J. Biol. Chem.*, 266: 15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO20080 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO20080 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO20080

The description below relates primarily to production of PRO20080 by culturing cells transformed or transfected with a vector containing PRO20080 nucleic acid. It is, of course, contemplated that alternative methods, which are well known in the art, may be employed to prepare PRO20080. For instance, the PRO20080 sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO20080 may be chemically synthesized separately and combined using chemical or enzymatic methods to produce the full-length PRO20080.

1. Isolation of DNA Encoding PRO20080

DNA encoding PRO20080 may be obtained from a cDNA library prepared from tissue believed to possess the PRO20080 mRNA and to express it at a detectable level. Accordingly, human PRO20080 DNA can be conveniently obtained from a cDNA library prepared from human tissue, such as described in the Examples. The PRO20080-encoding gene may also be obtained from a genomic library or by known synthetic procedures (e.g., automated nucleic acid synthesis).

Libraries can be screened with probes (such as antibodies to the PRO20080 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO20080 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO20080 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO20080-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published May 2, 1985); Kluyveromyces hosts (U.S. Pat. No. 4,943, 529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; yarrowia (EP 402,226); *Pichia pastoris* (EP 183,070; Sreekrishna et al., *J. Basic Microbiol.*, 28:265-278 [19881]; Candida; *Trichoderma reesia* (EP 244,234); *Neurospora crassa* (Case et al., *Proc. Natl. Acad. Sci. USA*, 76:5259-5263 [19791]); Schwanniomyces such as Schwanniomyces occidentalis (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs*, 269 (1982).

Suitable host cells for the expression of glycosylated PRO20080 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CVI line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO20080 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO20080 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO20080-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO20080-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4- [Jones, *Genetics,* 85:12 (1977)].

Expression and cloning vectors usually contain a promoter operably linked to the PRO20080-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO20080.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO20080 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO20080 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO20080 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO20080.

Still other methods, vectors, and host cells suitable for adaptation to the synthesis of PRO20080 in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO20080 polypeptide or against a synthetic peptide based on the DNA sequences provided herein or against exogenous sequence fused to PRO20080 DNA and encoding a specific antibody epitope.

5. Purification of Polypeptide

Forms of PRO20080 may be recovered from culture medium or from host cell lysates. If membrane-bound, it can be released from the membrane using a suitable detergent solution (e.g. Triton-X 100) or by enzymatic cleavage. Cells employed in expression of PRO20080 can be disrupted by various physical or chemical means, such as freeze-thaw cycling, sonication, mechanical disruption, or cell lysing agents.

It may be desired to purify PRO20080 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO20080. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular PRO20080 produced.

E. Tissue Distribution

The location of tissues expressing the PRO20080 can be identified by determining mRNA expression in various human tissues. The location of such genes provides information about which tissues are most likely to be affected by the stimulating and inhibiting activities of the PRO20080 polypeptides. The location of a gene in a specific tissue also provides sample tissue for the activity blocking assays discussed below.

As noted before, gene expression in various tissues may be measured by conventional Southern blotting, Northern blotting to quantitate the transcription of mRNA (Thomas, *Proc. Natl. Acad. Sci. USA,* 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a PRO20080 polypeptide or against a synthetic peptide based on the DNA sequences encoding the PRO20080 polypeptide or against an exogenous sequence fused to a DNA encoding a PRO20080 polypeptide and encoding a specific antibody epitope. General techniques for generating antibodies, and special protocols for Northern blotting and in situ hybridization are provided below.

F. Antibody Binding Studies

The activity of the PRO20080 polypeptides can be further verified by antibody binding studies, in which the ability of anti-PRO20080 antibodies to inhibit the effect of the PRO20080 polypeptides, respectively, on tissue cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

G. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see, e.g., Small et al., *Mol. Cell. Biol.* 5: 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology*, above, 3.15, 6.3.

A proliferative T cell response in an MLR assay may be due to direct mitogenic properties of an assayed molecule or to external antigen induced activation. Additional verification of the T cell stimulatory activity of the PRO20080 polypeptides can be obtained by a costimulation assay. T cell activation requires an antigen specific signal mediated through the T-cell receptor (TCR) and a costimulatory signal mediated through a second ligand binding interaction, for example, the B7 (CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a T cell deactivating effect. Chambers, C. A. and Allison, J. P., *Curr. Opin. Immunol.* (1997) 9:396. Schwartz, R. H., *Cell* (1992) 71:1065; Linsey, P. S. and Ledbetter, J. A., *Annu. Rev. Immunol.* (1993) 11:191; June, C. H. et al, *Immunol. Today* (1994) 15:321; Jenkins, M. K., *Immunity* (1994) 1:405. In a costimulation assay, the PRO20080 polypeptides are assayed for T cell costimulatory or inhibitory activity.

PRO20080 polypeptides, as well as other compounds of the invention, which are stimulators (costimulators) of T cell proliferation and agonists, e.g., agonist antibodies, thereto as determined by MLR and costimulation assays, for example, are useful in treating immune related diseases characterized by poor, suboptimal or inadequate immune function. These diseases are treated by stimulating the proliferation and activation of T cells (and T cell mediated immunity) and enhancing the immune response in a mammal through administration of a stimulatory compound, such as the stimulating PRO20080 polypeptides. The stimulating polypeptide may, for example, be a PRO20080 polypeptide or an agonist antibody thereof.

Direct use of a stimulating compound as in the invention has been validated in experiments with 4-1 BB glycoprotein, a member of the tumor necrosis factor receptor family, which binds to a ligand (4-I BBL) expressed on primed T cells and signals T cell activation and growth. Alderson, M. E. et al., *J. Immunol.* (1994) 24:2219.

The use of an agonist stimulating compound has also been validated experimentally. Activation of 4-1BB by treatment with an agonist anti-4-1BB antibody enhances eradication of tumors. Hellstrom, I. and Hellstrom, K. E., *Crit. Rev. Immunol.* (1998) 18:1. Immunoadjuvant therapy for treatment of tumors, described in more detail below, is another example of the use of the stimulating compounds of the invention.

An immune stimulating or enhancing effect can also be achieved by antagonizing or blocking the activity of a PRO20080 which has been found to be inhibiting in the MLR assay. Negating the inhibitory activity of the compound produces a net stimulatory effect. Suitable antagonists/blocking compounds are antibodies or fragments thereof which recognize and bind to the inhibitory protein, thereby blocking the effective interaction of the protein with its receptor and inhibiting signaling through the receptor. This effect has been validated in experiments using anti-CTLA-4 antibodies which enhance T cell proliferation, presumably by removal of the inhibitory signal caused by CTLA-4 binding. Walunas, T. L. et al, *Immunity* (1994) 1:405.

On the other hand, PRO20080 polypeptides, as well as other compounds of the invention, which are direct inhibitors of T cell proliferation/activation or lymphokine secretion, can be directly used to suppress the immune response. These compounds are useful to reduce the degree of the immune response and to treat immune related diseases characterized by a hyperactive, superoptimal, or autoimmune response. This use of the compounds of the invention has been validated by the experiments described above in which CTLA-4 binding to receptor B7 deactivates T cells. The direct inhibitory compounds of the invention function in an analogous manner. The use of compound which suppress vascular permeability would be expected to reduce inflammation. Such uses would be beneficial in treating conditions associated with excessive inflammation.

Alternatively, compounds, e.g., antibodies, which bind to stimulating PRO20080 polypeptides and block the stimulating effect of these molecules produce a net inhibitory effect and can be used to suppress the T cell mediated immune response by inhibiting T cell proliferation/activation and/or lymphokine secretion. Blocking the stimulating effect of the polypeptides suppresses the immune response of the mammal. This use has been validated in experiments using an anti-IL2 antibody. In these experiments, the antibody binds to IL2 and blocks binding of IL2 to its receptor thereby achieving a T cell inhibitory effect.

H. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology,* 2nd ed., W. E. Paul ed., Raven Press, NY, 1989, 889-992. A suitable procedure is described in detail in *Current Protocols in Immunology*, above, unit 4.4. Other transplant rejection models which can be used to test the compounds of the invention are the allogeneic heart transplant models described by Tanabe, M. et al, *Transplantation* (1994) 58:23 and Tinubu, S. A. et al, *J. Immunol*. (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S. and Schwarz, T, *Immun. Today* 19 (1): 37-44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in *Current Protocols in Immunology*, above, units 15.5. See also the model using a monoclonal antibody to CD18 and VLA-4 integrins described in Issekutz, A. C. et al., *Immunology* (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al, *Am. J. Respir. Cell Mol. Biol.* (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al, *Nat. Med*. (1997) 3:183, in which the mice demonstrate histopathologic skin lesions resembling psoriasis. Another suitable model is the human skin/scid mouse chimera prepared as described by Nickoloff, B. J. et al, *Am. J. Path*. (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cel. Biol.* 3, 1803-18141 [1983]); sperm-mediated gene transfer (Lavitrano et al., *Cell* 57, 717-7311989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to the PRO20080 polypeptide, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

1. ImmunoAdjuvant Therapy

In one embodiment, the immunostimulating compounds of the invention can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., (1996) *Proc. Natl. Acad. Sci. USA,* 93:7149. It has been shown that costimulation of T cells induces tumor regression and an antitumor response both in vitro and in vivo. Melero, I. et al., *Nature Medicine* (1997) 3:682; Kwon, E. D. et al., *Proc. Natl. Acad. Sci. USA* (1997) 94: 8099; Lynch, D. H. et al, *Nature Medicine* (1997) 3:625; Finn, O. J. and Lotze, M. T., *J. Immunol.* (1998) 21:114. The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

J. Screening Assays for Drug Candidates

Screening assays for drug candidates are designed to identify compounds that bind to or complex with the polypeptides encoded by the genes identified herein or a biologically active fragment thereof, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art. All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labelled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature (London)* 340, 245-246 (1989); Chien et al., *Proc. Natl. Acad. Sci. USA* 88, 9578-9582 (1991)] as disclosed by Chevray and Nathans, *Proc. Natl. Acad. Sci. USA* 89, 5789-5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

K. Compositions and Methods for the Treatment of Immune Related Diseases

The compositions useful in the treatment of immune related diseases include, without limitation, proteins, antibodies, small organic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

These molecules can be identified by any or any combination of the screening assays discussed above and/or by any other screening techniques well known for those skilled in the art.

L. Anti-PRO20080 Antibodies

The present invention further provides anti-PRO20080 antibodies. Exemplary antibodies include polyclonal, monoclonal, humanized, bispecific, and heteroconjugate antibodies.

1. Polyclonal Antibodies

The anti-PRO20080 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO20080 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO20080 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO20080 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO20080. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO20080 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368,812-13 (1994); Fishwild et al, Nature Biotechnology 14, 845-51 (1996); Neuberger, Nature Biotechnology 14, 826 (1996); Lonberg and Huszar, Intern. Rev. Immunol. 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO20080, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies may bind to two different epitopes on a given PRO20080 polypeptide herein. Alternatively, an anti-PRO20080 polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO20080 polypeptide. Bispecific antibodies may also be used to localize cytotoxic agents to cells which express a particular PRO20080 polypeptide. These antibodies possess a PRO20080-binding arm and an arm which binds a cytotoxic agent or a radionuclide chelator, such as EOTUBE, DPTA, DOTA, or TETA. Another bispecific antibody of interest binds the PRO20080 polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design.* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

M. Pharmaceutical Compositions

The active PRO20080 molecules of the invention (e.g., PRO20080 polypeptides, anti-PRO20080 antibodies, and/or variants of each) as well as other molecules identified by the screening assays disclosed above, can be administered for the treatment of immune related diseases, in the form of pharmaceutical compositions.

Therapeutic formulations of the active PRO20080 molecule, preferably a polypeptide or antibody of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

Compounds identified by the screening assays disclosed herein can be formulated in an analogous manner, using standard techniques well known in the art.

Lipofections or liposomes can also be used to deliver the PRO20080 molecule into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active PRO20080 molecules may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations or the PRO20080 molecules may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

N. Methods of Treatment

It is contemplated that the polypeptides, antibodies and other active compounds of the present invention may be used to treat various immune related diseases and conditions, such as T cell mediated diseases, including those characterized by infiltration of inflammatory cells into a tissue, stimulation of T-cell proliferation, inhibition of T-cell proliferation, increased or decreased vascular permeability or the inhibition thereof.

Exemplary conditions or disorders to be treated with the polypeptides, antibodies and other compounds of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rhematoid nodules.

Juvenile chronic arthritis is a chronic idiopathic inflammatory disease which begins often at less than 16 years of age. Its phenotype has some similarities to RA; some patients which are rhematoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barré syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis; and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative. Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate T cells can be utilized therapeutically to enhance the immune response to infectious agents), diseases of immunodeficiency (molecules/derivatives/agonists) which stimulate T cells can be utilized therapeutically to enhance the immune response for conditions of inherited, acquired, infectious induced (as in HIV infection), or iatrogenic (i.e., as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response have utility in vivo in enhancing the immune response against neoplasia. Molecules which enhance the T lymphocyte proliferative response (or small molecule agonists or antibodies that affected the same receptor in an agonistic fashion) can be used therapeutically to treat cancer.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The compounds of the present invention, e.g., polypeptides or antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation (intranasal, intrapulmonary) routes. Intravenous or inhaled administration of polypeptides and antibodies is preferred.

In immunoadjuvant therapy, other therapeutic regimens, such administration of an anti-cancer agent, may be combined with the administration of the proteins, antibodies or compounds of the instant invention. For example, the patient to be treated with a the immunoadjuvant of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the immunoadjuvant or may be given simultaneously therewith. Additionally, an anti-estrogen compound such as tamoxifen or an anti-progesterone such as onapristone (see, EP 616812) may be given in dosages known for such molecules.

It may be desirable to also administer antibodies against other immune disease associated or tumor associated antigens, such as antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of the disease, about 1 μg/kg to 15 mg/kg (e.g., 0.1-20 mg/kg) of polypeptide or antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

O. Articles of Manufacture

In another embodiment of the invention, an article of manufacture containing materials (e.g., comprising a PRO20080 molecule) useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. An instruction or label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

P. Diagnosis and Prognosis of Immune Related Disease

Cell surface proteins, such as proteins which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, or another immune related disease, can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding a Human PRO20080

The extracellular domain (ECD) sequences (including the secretion signal sequence, if any) from about 950 known secreted proteins from the Swiss-Prot public database were used to search sequence databases. The databases included public databases (e.g., GenBank) In this instance, genomic DNA sequence from GenBank was analyzed using the gene preditiction program GENSCAN, licenced from Stanford University. GENSCAN analysis predicts gene coding regions, creating sequences which can be subjected to the ECD search. The search was performed using the computer program BLAST or BLAST2 [Altschul et al., *Methods in Enzymology*, 266:460-480 (1996)] as a comparison of the ECD protein sequences to a 6 frame translation of the sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.) if necessary.

A consensus sequence is herein designated DNA145436.

Based on the DNA 145436 consensus sequence, oligonucleotides were synthesized: 1) to identify by PCR a cDNA library that contained the sequence of interest, and 2) for use as probes to isolate a clone of the full-length coding sequence for PRO20080. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:

```
forward PCR primer                  (SEQ ID NO:3)
5'-GAGAGAAGGTCAACTTCATCACTTGGCTTTTC-3' reverse PCR primer                  (SEQ ID NO:4)
5'-CTGCAGGAAACTCCAGGGGAAGAGTTACT-3'
```

Additionally, a synthetic oligonucleotide hybridization probe was constructed from the consensus DNA 145436 sequence which had the following nucleotide sequence hybridization probe
5'-CTTCACCCAGTCCTACTCCCTGCAACT-CAGCAACCTGAAGATGGAAGACA-3' (SEQ ID NO:5)

A pool of 50 different human cDNA libraries from various tissues was used in cloning. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD;

pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO20080 polypeptide (designated herein as DNA 161000-2896 [FIG. 1, SEQ ID NO: 1]) and the derived protein sequence for that PRO20080 polypeptide.

The full length clone identified above contained a single open reading frame with an apparent translational initiation site at nucleotide positions 62-64 and a stop signal at nucleotide positions 1058-1060 (FIG. 1, SEQ ID NO:1). The predicted polypeptide precursor is 332 amino acids long, has a calculated molecular weight of approximately 37345 daltons and an estimated pI of approximately 6.72. Analysis of the full-length PRO20080 sequence shown in FIG. 2 (SEQ ID NO:2) evidences the presence of a variety of important polypeptide domains as shown in FIG. 2, wherein the locations given for those important polypeptide domains are approximate as described above. PRO20080 amino acid sequence has 22% identity with CD84, 14% identity with SLAM and 11% identity with 2B4.

DNA161000-2896 was then deposited under the terms of the Budapest Treaty with the American Type Culture Collection, 10801 University Blvd., Manassas, Va. 20110-2209, USA (ATCC). Clone DNA161000-2896 has been deposited with ATCC on Apr. 18, 2000 and is assigned ATCC deposit number PTA-1731.

Example 2

Expression of PRO20080 in Multiple Human Tissues

Multiple tissue Northern Blots were obtained from Clontech (Palo Alto, Calif.). These blots were hybridized with a probe corresponding to the full length PRO20080 cDNA made by random primer labeling with $^{32}$P-γATP label. Blots were washed 3×with 2×SSC/0.2% SDS and 1×with 0.2×SSC/0.1%SDS at 42 C. The blots were then exposed to X-OMAT film with intensifying screens for overnight. The result is shown in FIG. 3. This shows that PRO20080 receptor is expressed highly in spleen and lymph node, with lower level of PRO20080 espression observed in thymus and bone marrow, with little expression in fetal liver. No expression was detected in brain, heart, colon or lung.

Example 3

Expression of PRO20080 in Multiple Human Cell Lines

Cell surface expression analysis of PRO20080 was performed by washing 1×10$^6$ cells in 1% FBS/PBS. An ALEXA-488 labeled monoclonal antibody raised against the extracellular domain of PRO20080 was used to detect surface staining on cell lines at a concentration of 1 ug per million cells. Cells were then washed again and analyzed by flow cytometry. All of the T cell derived lines such as Jurkat, MOLT3 and MOLT4 were positive for cell surface staining of PRO20080. The B cell lines that tested positive for PRO20080 expression were the Raji, Ramos and Daudi lines, with no detection of PRO20080 in the remainder of the B cell lines. This is shown in FIG. 4.

Example 4

Increased Expression of PRO20080 Upon Stimulation

Figure 5:
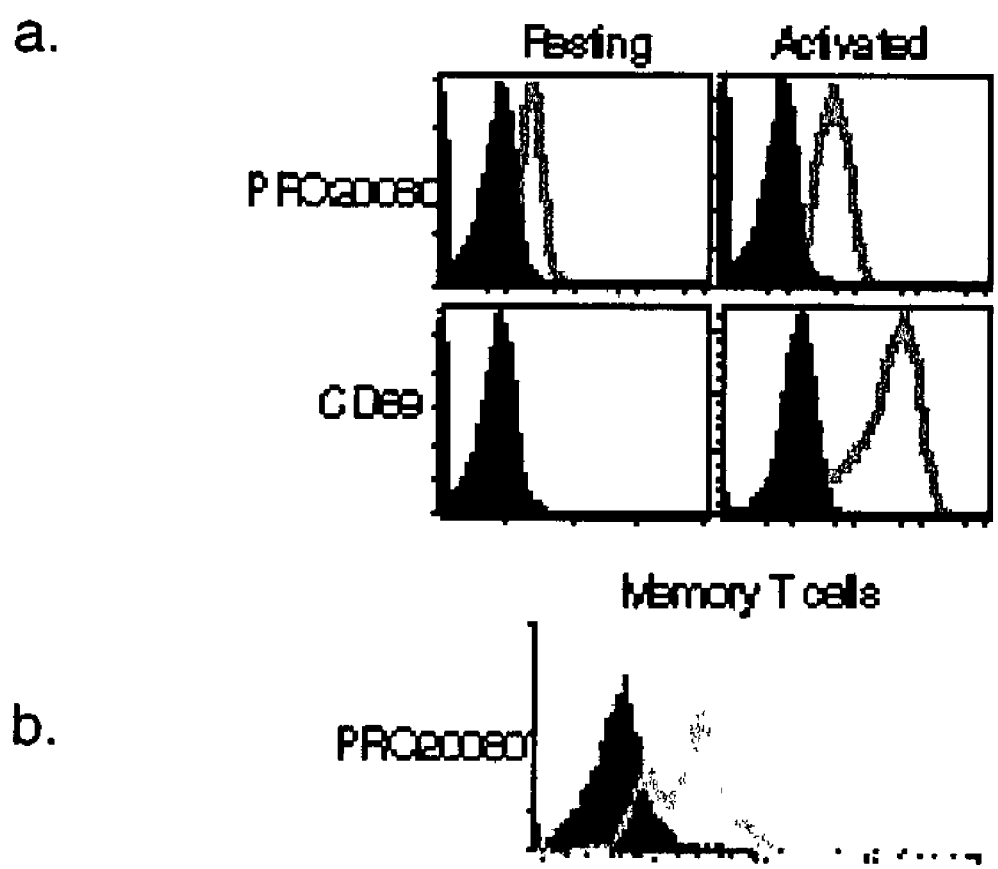
FIG. 5a shows the expression of PRO20080 on human peripheral T cells.
FIG. 5b shows high expression of PRO20080 on CD4+ CD45RO+memory Tcells.

Cell surface expression was detected by FACS analysis on isolated human peripheral T cells, as shown in FIG. 5. Human T cells were activated with plate-bound anti-CD3 antibody (coated at 0.1 ug/ml; Pharmingen) and anti-CD28 antibody (coated at 1 ug/ml;Pharmingen). 0.5×10$^6$ cells were plated per well. Both resting and activated T cells were then analyzed for expression of PRO20080 or CD69 at 24 and 48 hours by flow cytometry. PRO20080 expression was detected using the ALEXA-488 labeled monoclonal antibody raised against the extracellular domain of PRO20080 as described in Example 3. CD69, an activation marker, was detected using by flow cytometry using a FITC-labeled antibody (Pharmingen). Co-stimulation of isolated T cells with anti-CD3 and anti-CD28 antibody led to increased expression of PRO20080 on the cell surface as determined by FACS analysis at 24 hours (data not shown) and even greater expression at 48 hours post costimulation (FIG. 5a). High expression of PRO20080 on the surface of CD4+CD45RO+memory T cells without co-stimulation was also determined (FIG. 5b).

Example 5

Homotypic Binding of PRO20080

Figure 6:
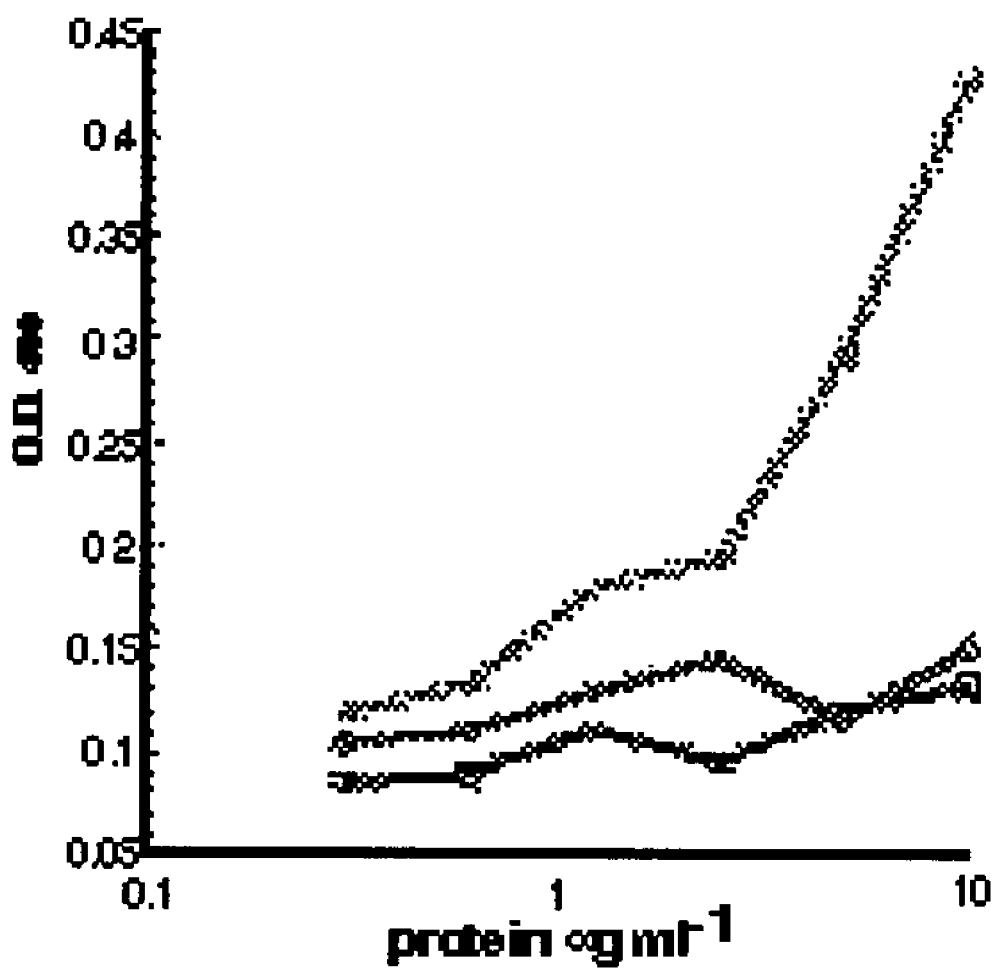
FIG. 6 shows an ELISA assay showing that labeled PRO20080 can bind to bound PRO20080.

To determine if PRO20080 interacts with itself in a PRO20080-PRO20080 association similar to SLAM, an ELISA assay was performed. Purified PRO20080-Fc fusion protein was coated onto a standard Nunc Maxisorb ELISA plate at a concentration of 2 µg/ml and increasing concentrations of biotinylated PRO20080 were incubated and subsequently washed. Binding of the biotinylated protein was detected using a streptavidin-HRP conjugate. It was determined that the biotinlyated PRO20080 can associate with the bound PRO20080 polypeptide and not with appropriate protein controls (FIG. 6).

Figure 7:
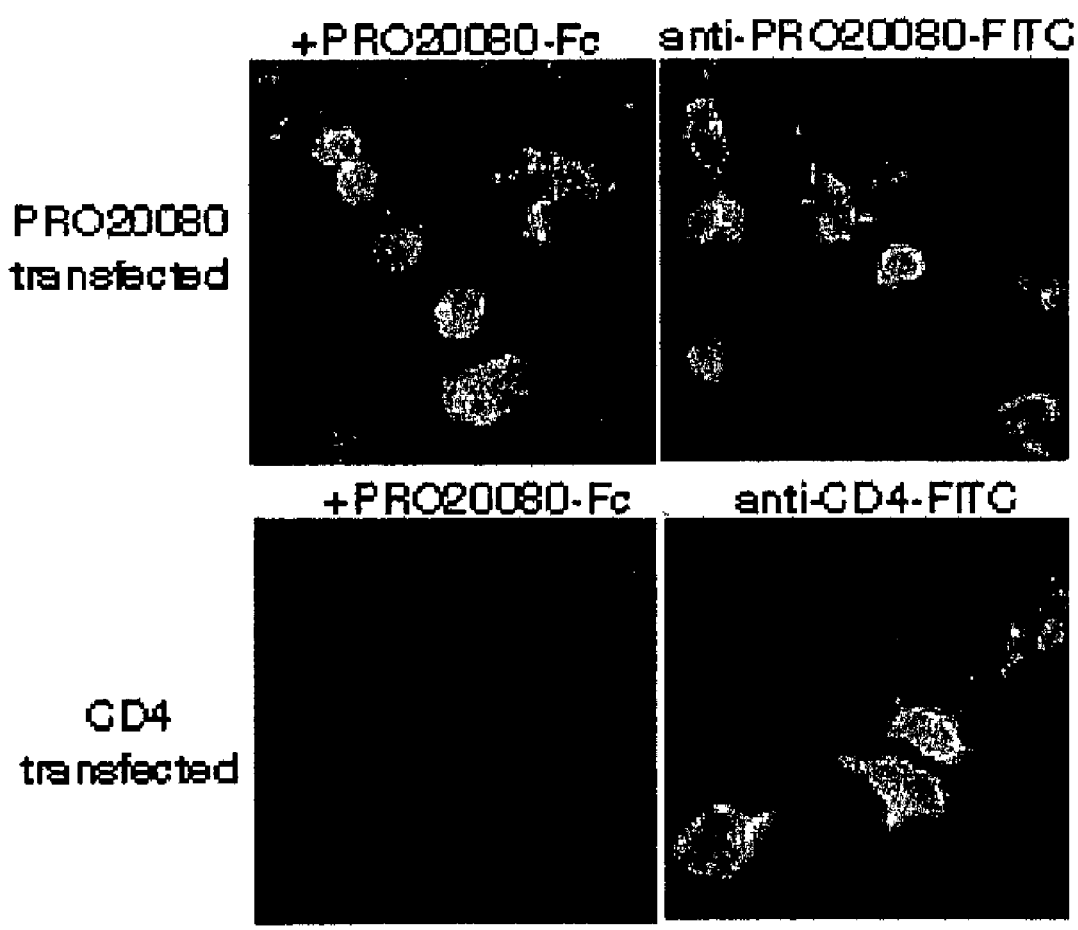
FIG. 7 shows homotypic binding of PRO20080 at the cell surface by immunofluoresence.

To determine if the ECD of PRO20080 can interact with a wild type PRO20080 on the cell surface, COS7 cells were transfected with wild type PRO20080 or human CD4, which contains an Ig domain, for use as a control. Forty-eight hours after transfection, the transfected cells washed and incubated with 5 µg/ml purified PRO20080 ECD-Fc fusion protein plus 5% normal goat serum. The treated cells were washed and fixed in 4% paraformadehyde for 15 minutes and then probed with a biotinlyated goat anti-human Fc antibody (Jackson Immunoreseach) at a dilution of 1:400. After a 30 minute incubation period, the fixed cells were washed and subsequently probed with a 1:400 dilution of Cy3-conjugated streptavidin label (Jackson Immunoresearch) for detection. Fluoresence was detected only in COS7 cells transfected with PRO20080, and not those COS7 cells transfected with CD 4, this demonstrates that soluble PRO20080 can associate with cell-bound PRO20080 in a specific manner, since no staining is observed on cells transfected with CD4, a receptor also containing Ig domain repeats. This is shown in FIG. 7.

Lastly, a BIAcore® assay was performed to determine if a His-tagged PRO20080 would associate with itself. The association rate can be determined by any method in which formation of the complex may be observed as a function of time. In the BIAcore® analysis, in which one measures the association of the protein to an protein that has been immobilized on a biosensor surface (reviewed by Rich & Myszka, Curr. Opin. Biotechnol. 11:54-61 (2000)). The homotypic interaction of His-tagged PRO20080 was calculated using BIAcore evaluation software version 3, and found to be a weak interaction, with a Kd of greater than 100 µM. This was a specific interaction as the His-tagged PRO20080 did not associate with a CD40 control protein. The Kd determined as determined by this assay is of the same order as the homotypic interaction of SLAM previously reported as 200 µM [Mavaddat et al., (2000) *J Biol Chem* 275(36): 28100-28109].

Taken together, the conclusion from these assays is that like SLAM, PRO20080 has self-interaction.

Example 6

Figure 8:
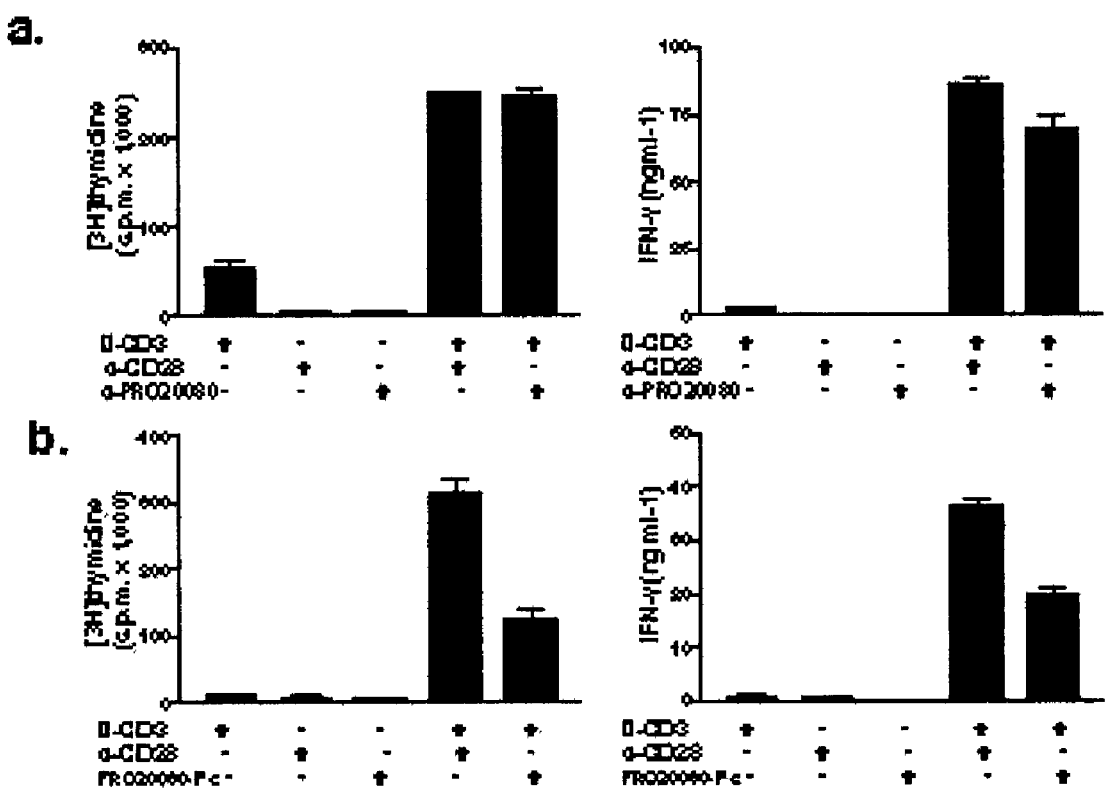
FIG. 8a shows the proliferation of T-cells and the production of INF-γ when T cells are stimulated with anti-PRO20080 antibody and anti-CD3 antibody.
FIG. 8b shows the proliferation of T-cells and the production of INF-γ when T cells are stimulated with PRO20080-Fc fusion molecule.

PRO20080-CD3 Costimulation Induces Tcell Proliferation and Increased INF-γ Production The crosslinking of SLAM and CD3 on T cells has a co-stimulatory effect, which is to increase proliferation of the T cells and the production of INF-γ. To determine if PRO20080 has a similar effect, human peripheral T cells were isolated and co-stimulated with an anti-PRO20080 antibody and a suboptimal dose of anti-CD3 antibody. Nunc Maxisorp 96-well plates were coated over night with 0.111 g ml anti-CD3 antibody (Pharmingen), 1 µg ml anti-CD28 (Pharmingen), or 1 µg ml anti-PRO20080 antibody generated against the extracellular domain of PRO20080. PRO20080-FC fusion protein was coated at 5 ug/ml. Human CD4+ T cells were purified using anti-CD4 beads and AutoMacs sorting from whole blood. For the costimulation assay $0.5 \times 10^6$ T cells were plated per well in triplicate. On the third day, post-costimulation, supernatant was removed for cytokine analysis of IFN-γ or IL-4 (by ELISA or Luminex-(Upstate Biotechnology)) and the cells were pulsed for 16 hours with [3H]thymidine to measure proliferation. This co-stimulation induced a substantial increase in proliferation comparable with with the increase in proliferation induced by the co-stimulation of anti-CD3 and anti-CD28 treatment. Anti-PRO20080 antibody treatment alone did not induce proliferation. Anti-CD3 antibody treatment alone also did not induce proliferation. This is shown in FIG. 8a.

INF-γ production in the removed supernatant was measured, and was found to have significantly increased over untreated cells or cells treated with anti-PRO20080 antibody or anti-CD3 antibody alone. The increase in INF-γ production upon co-stimulation with anti-PRO20080 antibody and anti-CD3 antibody was comparable to the increase in INF-γ production produced by co-stimulation with anti-CD3 antibody and anti-CD28 antibody. Treatment with anti-PRO20080 antibody alone did not induce any detectable increase in INF-γ production. This is shown in FIG. 8b.

Nonspecific induction of proliferation due to contaminants was ruled out with the use of boiled anti-PRO20080 and PRO20080 preps. No T cell proliferation was observed under these conditions (data not shown).

Example 7

PRO20080 Interacts with SAP

SLAM family members contain from two to four SAP binding motifs of the consensus (TxYxxV/I), where x can be any amino acid. SAP binds to non-phosphorylated and phosphorylated forms of SLAM, but greater amounts of SAP binding is seen when SLAM is phosphorylated. SLAM also binds the intracellular proteins SHP1 and SHP2, as well as binding SAP [Castro et al., (1999) *J. Immunol.* 163(11): 5860-5870, Lewis et al., (2001) *Clin Immunol* 100(1): 15-23, Shlapatska et al., (2001) *J. Immunol* 166 (9: 5480-5487]. PRO20080 contains two SAP binding motifs in the intracellular domain of the molecule (FIG. 2), and to determine if SAP, SHP1 and SHP2 bound to PRO20080, $10^7$ Jurkat T cells were treated with pervanadate for 15 minutes at 37° C. and lysed in RIPA buffer with 1% NP-40 and protease and phosphatase inhibitors. Lysates were pre-cleared with 10 µg/ml IgG1 and protein G; then PRO20080 was immunoprecipitated using 10 µg of a mixture of IgG1 monoclonal antibodies raised against the extracellular domain of PRO20080. All samples were then run on a 4-20% SDS-PAGE gel (Novagen Madison, Wis.). Association of SAP was detected by Western blotting using an antibody raised against full length SAP in rabbit (Santa Cruz Biotechnology Santa Cruz, Calif.). SAP was detected using 2 µg/ml antibody diluted in 5% powdered milk. These results of PRO20080 Western blotting are shown in FIG. 9a. There was no PRO20080 association with SAP in untreated cells. PRO20080 did associate with SAP in pervanadate treated cells, implying a phosphorylation-dependant interaction. SHP1 and SHP2 are expressed in Jurkat cells, but no interaction with PRO20080 was detected under any of the conditions tested. Therefore, PRO20080 interacts with SAP, but not with SHP1 or SHP2, making the signal transduction pathway of PRO20080 differ signifcantly from that of SLAM.

Example 8

PRO20080 Phosphorylation Upon Co-stimulation

To examine the signaling events surrounding PRO20080 during co-stimulation, a phosphorylation timecourse experiment was performed. For the Jurkat timcourse, cells were first incubated with anti-CD3 and anti-PRO20080 antibodies at 0.5 µg per $10^6$ cells (Pharmingen). Cells were then washed, let to rest in PBS, then stimulated with goat anti-mouse Fc antibody (Jackson Immunoresearch) at 0.1 µg per $10^6$ cells to crosslink the receptors. Cross linking times began with a minimum 30 seconds to a maximum of 10 minutes. It was found that PRO20080 was phosphorylated within 30 seconds (FIG. 9b).

Phosphorylation of PRO20080 was also examined in isolated human T cells. Human T cells were isolated by AutoMACS sorting of CD4 positive cells. 400 million cells were used per condition. In similar conditions used for the Jurkat cells, PRO20080 is phosphorylated upon CD3 and PRO20080 cross linking, as shown by immunoprecipitation of PRO20080 and subsequent western blotting with an anti-phosphotyrosine antibody. In detecting for SAP, it was found that SAP does not associate with PRO20080 in untreated human T cells, but does associate with phosphorylated PRO20080. As in the Jurkat cell line, SHP1 and SHP2 do not associate with PRO20080 even though both SHP1 and SHP2 are expressed (FIG. 9c). These results suggest a SAP dependant, but SHP1/SHP2 independant pathway, different from SLAM.

Example 9

PRO20080 and Delayed Type Hypersensitive Response

As mentioned previously SLAM plays a role in Th1 cell response. To determine if PRO20080 also has a role in Th1 cell response, the murine homologue of PRO20080 was cloned, and used in in vivo experiments to test for delayed type hypersenstivity (DTH). For mouse studies CD4+ T cells were isolated from the spleen by AutoMacs sorting, and 1, 5, and 10 ug ml of murine PRO20080 was used for stimulation. Anti-mouse CD3 antibody and anti-mouse CD28 antibody were used at similar concentrations as for the human assays (0.1 ug ml-1; 1 ug ml-1;Pharmingen). Cells were stimulated for three days and a fraction of the supernatant was removed from the wells to test for cytokine expression and cells were pulsed with [3H]thymidine in the final 16 hours of culture to determine proliferation levels. Similar results were found with co-stimulation involving murine PRO20080-Fc fusion protein and human PRO20080.

Figure 10:
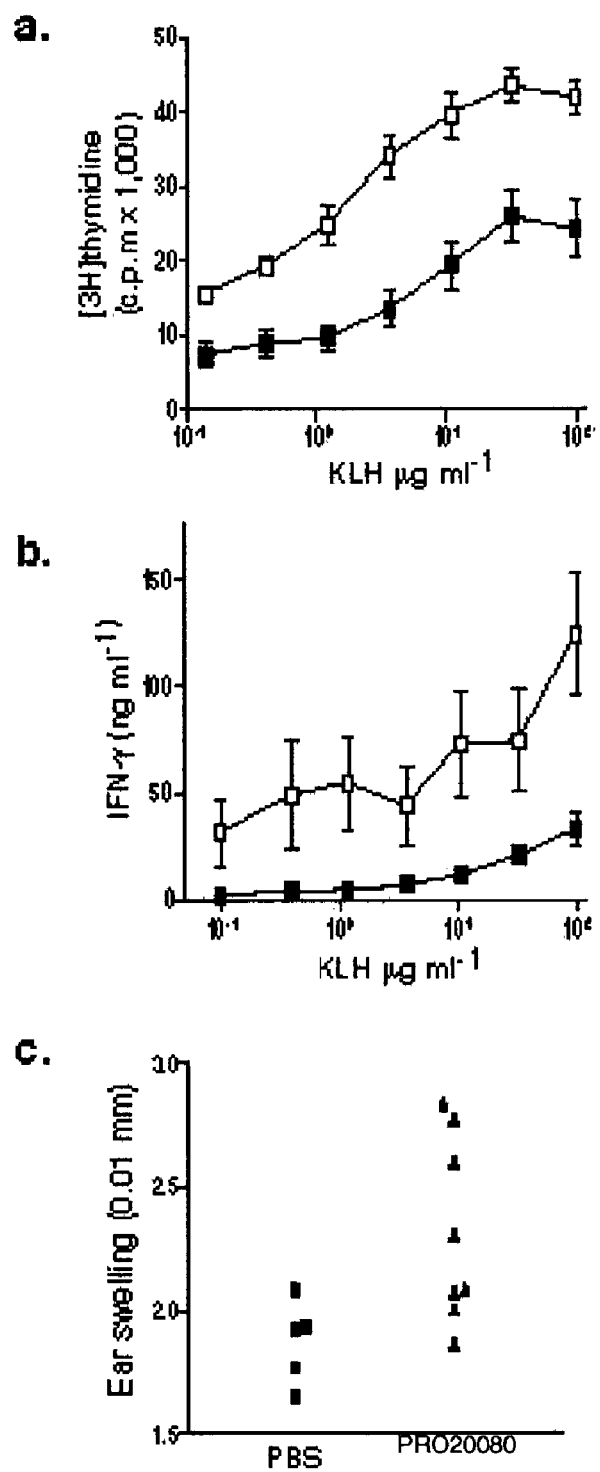
FIG. 10a shows the effect of the murine homologue of PRO20080 on T cell proliferation in vivo.
FIG. 10b shows the effect of the murine homologue of PRO20080 on INF-γ production in vivo.
FIG. 10c shows the effect of murine homologue of PRO20080 in a delayed-type hypersensitivity response as measured by ear swelling.

Mice were injected in the footpad with 100 μg keyhole-limpet hemocyanin (KLH) 1:1 in CFA. Mice were also injected IP every other day with 100 μg murine PRO20080-Fc or saline. On day 9, draining lymph nodes were collected from the mice and cells were incubated with KLH. On the third day, supernatant was removed for cytokine analysis and the cells were pulsed with [3H]thymidine to measure proliferation. This result is shown in FIG. 10a (proliferation) and FIG. 10b (IFN-γ increase). Lymphocytes from murine PRO20080-Fc treated mice increased in proliferation in response to KLH challenge. IFN-γ production was also increased 2-4 fold.

The increase in IFN-γ is proposed to modifiy T cell response to a Th I response, and possibly DTH. For DTH experiments, mice were injected with 100 μg of KLH (1:1 mixture with CFA) in the base of the tail. Mice were injected IP with 100 μg of the murine PRO20080-Fc or saline on day 0, 2, 5, 6, and 7. On day 6 mice were injected with 150 μg of KLH in the left ear and saline in the right ear (25 μl volume). Ear swelling was measured on day 8, 48 hours after ear injection. The difference in size between the left and right ear was plotted, and is shown in FIG. 10c. These results suggest that the murine PRO20080 is involved in DTH, a Th1 response.

Example 10

Preparation of Antibodies that Bind PRO20080

This example illustrates preparation of monoclonal antibodies which can specifically bind PRO20080. In this instance, antibodies were made to the ECD of PRO20080, from about amino acid 13 to about amino acid 228 of FIG. 2 [SEQ ID NO:2].

Techniques for producing the monoclonal antibodies are known in the art and are described, for instance, in Goding, supra. Selection of the immunogen can be made by the skilled artisan without undue experimentation.

Mice, such as Balb/c, are immunized with the PRO20080 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO20080 antibodies.

After a suitable antibody titer has been detected, the animals "positive" for antibodies can be injected with a final intravenous injection of PRO20080. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO20080. Determination of "positive" hybridoma cells secreting the desired monoclonal antibodies against PRO20080 is within the skill in the art.

The positive hybridoma cells can be injected intraperitoneally into syngeneic Balb/c mice to produce ascites containing the anti-PRO20080 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed. These antibodies were useful in the identification of PRO20080 in cell expression analysis, ELISA, and Western blotting.

Example 11

Use of PRO20080 as a Hybridization Probe

The following method describes use of a nucleotide sequence encoding PRO20080 as a hybridization probe.

DNA comprising the coding sequence of full-length or mature PRO20080 as disclosed herein is employed as a probe to screen for homologous DNAs (such as those encoding naturally-occurring variants of PRO20080) in human tissue cDNA libraries or human tissue genomic libraries.

Hybridization and washing of filters containing either library DNAs is performed under the following high stringency conditions. Hybridization of radiolabeled PRO20080-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO20080 can then be identified using standard techniques known in the art.

Example 12

Expression of PRO20080 in *E. coli*

This example illustrates preparation of an unglycosylated form of PRO20080 by recombinant expression in *E. coli*.

The DNA sequence encoding PRO20080 is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO20080 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO20080 protein can then be purified using a metal chelating column under conditions that allow tight binding of the protein.

PRO20080 may be expressed in *E. coli* in a poly-His tagged form, using the following procedure. The DNA encoding PRO20080 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate·2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO20080 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO20080 polypeptides disclosed herein were successfully expressed as described above.

Example 13

Expression of PRO20080 in Mammalian Cells

This example illustrates preparation of a potentially glycosylated form of PRO20080 by recombinant expression in mammalian cells.

The vector, pRK5 (see EP 307,247, published Mar. 15, 1989), is employed as the expression vector. Optionally, the PRO20080 DNA is ligated into pRK5 with selected restriction enzymes to allow insertion of the PRO20080 DNA using ligation methods such as described in Sambrook et al., supra. The resulting vector is called pRK5-PRO20080.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO20080 DNA is mixed with about 1 µg DNA encoding the VA RNA gene [Thimmappaya et al., *Cell,* 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO20080 polypeptide. The cultures containing transfected cells may undergo further incubation (in serum free medium) and the medium is tested in selected bioassays.

In an alternative technique, PRO20080 may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO20080 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO20080 can then be concentrated and purified by any selected method, such as dialysis and/or column chromatography.

In another embodiment, PRO20080 can be expressed in CHO cells. The pRK5-PRO20080 can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of PRO20080 polypeptide, the culture medium may be replaced with serum free medium. Preferably, the cultures are incubated for about 6 days, and then the conditioned medium is harvested. The medium containing the expressed PRO20080 can then be concentrated and purified by any selected method.

Epitope-tagged PRO20080 may also be expressed in host CHO cells. The PRO20080 may be subcloned out of the pRK5 vector. The subclone insert can undergo PCR to fuse in frame with a selected epitope tag such as a poly-his tag into a Baculovirus expression vector. The poly-his tagged PRO20080 insert can then be subcloned into a SV40 promoter/enhancer containing vector containing a selection marker such as DHFR for selection of stable clones. Finally, the CHO cells can be transfected (as described above) with the SV40 promoter/enhancer containing vector. Labeling may be performed, as described above, to verify expression. The culture medium containing the expressed poly-His tagged PRO20080 can then be concentrated and purified by any selected method, such as by $Ni^{2+}$-chelate affinity chromatography.

PRO20080 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3\times10^{-7}$ cells are frozen in an ampule for further growth and production as described below.

The ampules containing the plasmid DNA are thawed by placement into water bath and mixed by vortexing. The contents are pipetted into a centrifuge tube containing 10 mL of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2\times10^6$ cells/mL. On day 0, pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μl of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO20080 polypeptides disclosed herein were successfully expressed as described above.

Example 14

Expression of PRO20080 in Yeast

The following method describes recombinant expression of PRO20080 in yeast.

First, yeast expression vectors are constructed for intracellular production or secretion of PRO20080 from the ADH2/GAPDH promoter. DNA encoding PRO20080 and the promoter is inserted into suitable restriction enzyme sites in the selected plasmid to direct intracellular expression of PRO20080. For secretion, DNA encoding PRO20080 can be cloned into the selected plasmid, together with DNA encoding the ADH2/GAPDH promoter, a native PRO20080 signal peptide or other mammalian signal peptide, or, for example, a yeast alpha-factor or invertase secretory signal/leader sequence, and linker sequences (if needed) for expression of PRO20080.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO20080 can subsequently be isolated and purified by removing the yeast cells from the fermentation medium by centrifugation and then concentrating the medium using selected cartridge filters. The concentrate containing PRO20080 may further be purified using selected column chromatography resins.

Many of the PRO20080 polypeptides disclosed herein were successfully expressed as described above.

Example 15

Expression of PRO20080 in Baculovirus-Infected Insect Cells

The following method describes recombinant expression of PRO20080 in Baculovirus-infected insect cells.

The sequence coding for PRO20080 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO20080 or the desired portion of the coding sequence of PRO20080 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO20080 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO20080 are pooled and dialyzed against loading buffer.

Alternatively, purification of the IgG tagged (or Fc tagged) PRO20080 can be performed using known chromatography techniques, including for instance, Protein A or protein G column chromatography.

Many of the PRO20080 polypeptides disclosed herein were successfully expressed as described above.

Example 16

Purification of PRO20080 Polypeptides Using Specific Antibodies

Native or recombinant PRO2008 polypeptides may be purified by a variety of standard techniques in the art of protein purification. For example, pro-PRO20080 polypeptide, mature PRO20080 polypeptide, or pre-PRO20080 polypeptide is purified by immunoaffinity chromatography using antibodies specific for the PRO20080 polypeptide of interest. In general, an immunoaffinity column is constructed by covalently coupling the anti-PRO20080 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO20080 polypeptide by preparing a fraction from cells containing PRO20080 polypeptide in a soluble form. This preparation is derived by solubilization of the whole cell or of a subcellular fraction obtained via differential centrifugation by the addition of detergent or by other methods well known in the art. Alternatively, soluble PRO20080 polypeptide containing a signal sequence may be secreted in useful quantity into the medium in which the cells are grown.

A soluble PRO20080 polypeptide-containing preparation is passed over the immunoaffinity column, and the column is washed under conditions that allow the preferential absorbance of PRO20080 polypeptide (e.g., high ionic strength buffers in the presence of detergent). Then, the column is eluted under conditions that disrupt antibody/PRO20080 polypeptide binding (e.g., a low pH buffer such as approximately pH 2-3, or a high concentration of a chaotrope such as urea or thiocyanate ion), and PRO20080 polypeptide is collected.

Example 17

Drug Screening

This invention is particularly useful for screening compounds by using PRO20080 polypeptides or binding fragment thereof in any of a variety of drug screening techniques. The PRO20080 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO20080 polypeptide or fragment. Drugs are screened against such transformed cells in competitive binding assays. Such cells, either in viable or fixed form, can be used for standard binding assays. One may measure, for example, the formation of complexes between PRO20080 polypeptide or a fragment and the agent being tested. Alternatively, one can examine the diminution in complex formation between the PRO20080 polypeptide and its target cell or target receptors caused by the agent being tested.

Thus, the present invention provides methods of screening for drugs or any other agents which can affect a PRO20080 polypeptide-associated disease or disorder. These methods comprise contacting such an agent with an PRO20080 polypeptide or fragment thereof and assaying (I) for the presence of a complex between the agent and the PRO20080 polypeptide or fragment, or (ii) for the presence of a complex between the PRO20080 polypeptide or fragment and the cell, by methods well known in the art. In such competitive binding assays, the PRO20080 polypeptide or fragment is typically labeled. After suitable incubation, free PRO20080 polypeptide or fragment is separated from that present in bound form, and the amount of free or uncomplexed label is a measure of the ability of the particular agent to bind to PRO20080 polypeptide or to interfere with the PRO20080 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO20080 polypeptide, the peptide test compounds are reacted with PRO20080 polypeptide and washed. Bound PRO20080 polypeptide is detected by methods well known in the art. Purified PRO20080 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO20080 polypeptide specifically compete with a test compound for binding to PRO20080 polypeptide or fragments thereof. In this manner, the antibodies can be used to detect the presence of any peptide which shares one or more antigenic determinants with PRO20080 polypeptide.

Example 18

Rational Drug Design

The goal of rational drug design is to produce structural analogs of biologically active polypeptide of interest (i.e., a PRO20080 polypeptide) or of small molecules with which they interact, e.g., agonists, antagonists, or inhibitors. Any of these examples can be used to fashion drugs which are more active or stable forms of the PRO20080 polypeptide or which enhance or interfere with the function of the PRO20080 polypeptide in vivo (c.f., Hodgson, *Bio/Technology*, 9: 19-21 (1991)).

In one approach, the three-dimensional structure of the PRO20080 polypeptide, or of a PRO20080 polypeptide-inhibitor complex, is determined by x-ray crystallography, by computer modeling or, most typically, by a combination of the two approaches. Both the shape and charges of the PRO20080 polypeptide must be ascertained to elucidate the structure and to determine active site(s) of the molecule. Less often, useful information regarding the structure of the PRO20080 polypeptide may be gained by modeling based on the structure of homologous proteins. In both cases, relevant structural information is used to design analogous PRO20080 polypeptide-like molecules or to identify efficient inhibitors. Useful examples of rational drug design may include molecules which have improved activity or stability as shown by Braxton and Wells, *Biochemistry* 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO20080 polypeptide may be made available to perform such analytical studies as X-ray crystallography. In addition, knowledge of the PRO20080 polypeptide amino acid sequence provided herein will provide guidance to those employing computer modeling techniques in place of or in addition to x-ray crystallography.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed:

1. Isolated nucleic acid encoding a polypeptide comprising the polypeptide sequence shown in FIG. 2 (SEQ ID NO: 2), with or without the associated signal peptide from amino acids 1-13.

2. A vector comprising the nucleic acid of claim 1.

3. The vector of claim 2 operably linked to control sequences recognized by a host cell transformed with the vector.

4. An isolated host cell comprising the vector of claim 2.

5. The host cell of claim 4, wherein said cell is a CHO cell, an *E. coli* cell or a yeast cell.

6. A process for producing a PRO20080 polypeptide comprising culturing the host cell of claim 4 under conditions suitable for expression of said PRO20080 polypeptide and recovering said PRO20080 polypeptide from the cell culture.

* * * * *

UNITED STATES PATENT AND TRADEMARK OFFICE
CERTIFICATE OF CORRECTION

PATENT NO. : 7,419,799 B2 Page 1 of 1
APPLICATION NO. : 10/136574
DATED : September 2, 2008
INVENTOR(S) : Patricia A. Valdez et al.

It is certified that error appears in the above-identified patent and that said Letters Patent is hereby corrected as shown below:

On the front page, in the "Assignee": (73) delete the Assignee data and replace as follows:

-- (73) Assignee: Genentech, Inc., South San Francisco, CA (US) --

Signed and Sealed this

Twenty-fourth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,419,799 B2  Page 1 of 1
APPLICATION NO. : 10/136574
DATED : September 2, 2008
INVENTOR(S) : Patricia A. Valdez et al.

It is certified that error appears in the above-identified patent and that said Letters Patent is hereby corrected as shown below:

Item (63)
On the front page, please add the "Related Foreign Application Data" as follows:

-- PCT/US2001/27099 filed August 29, 2001 --

Signed and Sealed this

Second Day of June, 2009

JOHN DOLL
*Acting Director of the United States Patent and Trademark Office*

SEQUENCE LISTING

<160> NUMBER OF SEQ ID NOS: 5

<210> SEQ ID NO 1
<211> LENGTH: 1868
<212> TYPE: DNA
<213> ORGANISM: Homo Sapien

<400> SEQUENCE: 1

| | | | | |
|---|---|---|---|---|
| cagaagggca | aaaacattga | ctgcctcaag | gtctcaagca | ccagtcttca | 50 |
| ccgcggaaag | catgttgtgg | ctgttccaat | cgctcctgtt | tgtcttctgc | 100 |
| tttggcccag | ggaatgtagt | ttcacaaagc | agcttaaccc | cattgatggt | 150 |
| gaacgggatt | ctgggggagt | cagtaactct | tcccctggag | tttcctgcag | 200 |
| gagagaaggt | caacttcatc | acttggcttt | tcaatgaaac | atctcttgcc | 250 |
| ttcatagtac | cccatgaaac | caaaagtcca | gaaatccacg | tgactaatcc | 300 |
| gaaacaggga | aagcgactga | acttcaccca | gtcctactcc | ctgcaactca | 350 |
| gcaacctgaa | gatggaagac | acaggctctt | acagagccca | gatatccaca | 400 |
| aagacctctg | caaagctgtc | cagttacact | ctgaggatat | aagacaact | 450 |
| gaggaacata | caagttacca | atcacagtca | gctatttcag | aatatgacct | 500 |
| gtgagctcca | tctgacttgc | tctgtggagg | atgcagatga | caatgtctca | 550 |
| ttcagatggg | aggccttggg | aaacacactt | tcaagtcagc | caaacctcac | 600 |
| tgtctcctgg | gaccccagga | tttccagtga | acaggactac | acctgcatag | 650 |
| cagagaatgc | tgtcagtaat | ttatccttct | ctgtctctgc | ccagaagctt | 700 |
| tgcgaagatg | ttaaaattca | atatacagat | accaaaatga | ttctgtttat | 750 |
| ggtttctggg | atatgcatag | tcttcggttt | catcatactg | ctgttacttg | 800 |
| ttttgaggaa | aagaagagat | tccctatctt | tgtctactca | gcgaacacag | 850 |
| ggccccgcag | agtccgcaag | gaacctagag | tatgtttcag | tgtctccaac | 900 |
| gaacaacact | gtgtatgctt | cagtcactca | ttcaaacagg | gaaacagaaa | 950 |
| tctggacacc | tagagaaaat | gatactatca | caatttactc | cacaattaat | 1000 |
| cattccaaag | agagtaaacc | cacttttttcc | agggcaactg | cccttgacaa | 1050 |
| tgtcgtgtaa | gttgctgaaa | ggcctcagag | gaattcggga | atgacacgtc | 1100 |
| ttctgatccc | atgagacaga | acaaagaaca | ggaagcttgg | ttcctgttgt | 1150 |
| tcctggcaac | agaatttgaa | tatctaggat | aggatgatca | cctccagtcc | 1200 |
| ttcggactta | aacctgccta | cctgagtcaa | acacctaagg | ataacatcat | 1250 |
| ttccagcatg | tggttcaaat | aatatttttcc | aatccacttc | aggccaaaac | 1300 |
| atgctaaaga | taacacacca | gcacattgac | tctctctttg | ataactaagc | 1350 |
| aaatggaatt | atggttgaca | gagagtttat | gatccagaag | acaaccactt | 1400 |
| ctctcctttt | agaaagcagc | aggattgact | tattgagaaa | taatgcagtg | 1450 |
| tgttggttac | atgtgtagtc | tctggagttg | gatgggccca | tcctgataca | 1500 |
| agttgagcat | cccttgtctg | aaatgcttgg | gattagaaat | gtttcagatt | 1550 |
| tcaattttttt | ttcagatttt | ggaatatttg | cattatattt | agcggttgag | 1600 |
| tatccaaatc | caaaaatcca | aaattcaaaa | tgctccaata | agcatttccc | 1650 |
| ttgagtttca | ttgatgtcga | tgcagtgctc | aaaatctcag | attttggagc | 1700 |

```
aatttggata ttggattttt ggatttggga tgctcaactt gtacaatgtt          1750
tattagacac atctcctggg acatactgcc taacctttg gagccttagt           1800 ctcccagact gaaaaaggaa gaggatggta ttacatcagc tccattgttt          1850
gagccaagaa tctaagtc                                             1868
```

<210> SEQ ID NO 2
<211> LENGTH: 332
<212> TYPE: PRT
<213> ORGANISM: Homo Sapien

<400> SEQUENCE: 2

```
Met Leu Trp Leu Phe Gln Ser Leu Leu Phe Val Phe Cys Phe Gly
 1               5                  10                  15

Pro Gly Asn Val Val Ser Gln Ser Ser Leu Thr Pro Leu Met Val
                20                  25                  30

Asn Gly Ile Leu Gly Glu Ser Val Thr Leu Pro Leu Glu Phe Pro
                35                  40                  45

Ala Gly Glu Lys Val Asn Phe Ile Thr Trp Leu Phe Asn Glu Thr
                50                  55                  60

Ser Leu Ala Phe Ile Val Pro His Glu Thr Lys Ser Pro Glu Ile
                65                  70                  75

His Val Thr Asn Pro Lys Gln Gly Lys Arg Leu Asn Phe Thr Gln
                80                  85                  90

Ser Tyr Ser Leu Gln Leu Ser Asn Leu Lys Met Glu Asp Thr Gly
                95                 100                 105

Ser Tyr Arg Ala Gln Ile Ser Thr Lys Thr Ser Ala Lys Leu Ser
               110                 115                 120

Ser Tyr Thr Leu Arg Ile Leu Arg Gln Leu Arg Asn Ile Gln Val
               125                 130                 135

Thr Asn His Ser Gln Leu Phe Gln Asn Met Thr Cys Glu Leu His
               140                 145                 150

Leu Thr Cys Ser Val Glu Asp Ala Asp Asp Asn Val Ser Phe Arg
               155                 160                 165

Trp Glu Ala Leu Gly Asn Thr Leu Ser Ser Gln Pro Asn Leu Thr
               170                 175                 180

Val Ser Trp Asp Pro Arg Ile Ser Ser Glu Gln Asp Tyr Thr Cys
               185                 190                 195

Ile Ala Glu Asn Ala Val Ser Asn Leu Ser Phe Ser Val Ser Ala
               200                 205                 210

Gln Lys Leu Cys Glu Asp Val Lys Ile Gln Tyr Thr Asp Thr Lys
               215                 220                 225

Met Ile Leu Phe Met Val Ser Gly Ile Cys Ile Val Phe Gly Phe
               230                 235                 240

Ile Ile Leu Leu Leu Leu Val Leu Arg Lys Arg Arg Asp Ser Leu
               245                 250                 255

Ser Leu Ser Thr Gln Arg Thr Gln Gly Pro Ala Glu Ser Ala Arg
               260                 265                 270

Asn Leu Glu Tyr Val Ser Val Ser Pro Thr Asn Asn Thr Val Tyr
               275                 280                 285

Ala Ser Val Thr His Ser Asn Arg Glu Thr Glu Ile Trp Thr Pro
               290                 295                 300

Arg Glu Asn Asp Thr Ile Thr Ile Tyr Ser Thr Ile Asn His Ser
               305                 310                 315
```

```
Lys Glu Ser Lys Pro Thr Phe Ser Arg Ala Thr Ala Leu Asp Asn
            320                 325                 330

Val Val

<210> SEQ ID NO 3
<211> LENGTH: 32
<212> TYPE: DNA
<213> ORGANISM: Artificial Sequence
<220> FEATURE:
<223> OTHER INFORMATION: Synthetic oligonucleotide probe

<400> SEQUENCE: 3
gagagaaggt caacttcatc acttggcttt tc                              32

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 4
ctgcaggaaa ctccagggga agagttact                                  29

<210> SEQ ID NO 5
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 5
cttcacccag tcctactccc tgcaactcag caacctgaag atggaagaca            50
```